(12) United States Patent
Gerstner et al.

(10) Patent No.: US 9,844,417 B2
(45) Date of Patent: *Dec. 19, 2017

(54) MEDICAL TOOL KIT

(71) Applicant: Mobilize RRS LLC, Pittsford, NY (US)

(72) Inventors: Jeffrey D. Gerstner, Pittsford, NY (US); Robert Gerstner, New York, NY (US)

(73) Assignee: Mobilize RRS LLC, Pittsford, NY (US)

( * ) Notice: Subject to any disclaimer, the term of this patent is extended or adjusted under 35 U.S.C. 154(b) by 298 days.

This patent is subject to a terminal disclaimer.

(21) Appl. No.: 14/539,376

(22) Filed: Nov. 12, 2014

(65) Prior Publication Data

US 2015/0068942 A1 Mar. 12, 2015

Related U.S. Application Data

(63) Continuation-in-part of application No. 13/228,085, filed on Sep. 8, 2011, now Pat. No. 8,911,677.

(51) Int. Cl.
*A61B 50/33* (2016.01)
*A61B 50/30* (2016.01)
*A61L 2/10* (2006.01)
*A61B 17/00* (2006.01)
*A61B 50/00* (2016.01)

(52) U.S. Cl.
CPC ............. *A61B 50/33* (2016.02); *A61B 50/30* (2016.02); *A61B 2017/00734* (2013.01); *A61B 2050/005* (2016.02); *A61B 2050/0051* (2016.02); *A61B 2050/0056* (2016.02); *A61B 2050/0076* (2016.02); *A61B 2050/0078* (2016.02); *A61B 2050/3008* (2016.02); *A61L 2/10* (2013.01); *A61L 2202/16* (2013.01); *A61L 2202/182* (2013.01); *A61L 2202/24* (2013.01)

(58) Field of Classification Search
CPC .......... B01L 2200/18; A61L 2/08; A61L 2/10; A61L 2/24; A61L 2202/11; A61L 2202/18; A61L 2202/182; A61L 2202/24; A61B 50/30; A61B 50/33; A61B 2050/005–2050/0088; A61B 2017/00734; A61B 19/026; A61B 19/0264; A61B 19/0271

See application file for complete search history.

(56) References Cited

U.S. PATENT DOCUMENTS

2011/0011886 A1* 1/2011 Zaima ....................... A61L 2/26
222/1

* cited by examiner

*Primary Examiner* — Timothy Cleveland
(74) *Attorney, Agent, or Firm* — Woods Oviatt Gilman LLP; Katherine H. McGuire, Esq.

(57) ABSTRACT

A medical tool kit is provided for packaging, storing, and transporting medical instruments and tools of various types. The medical tool kit is capable of providing continuing sterilization to the medical instruments and tools kept inside the medical toot kit after the tool case is opened during its normal use in a medical procedure. The medical tool kit is further capable of emitting a GPS tracking signal to identify the location of an opened medical tool kit during an emergency as well as creating hands free communication between the user of the medical tool kit and local emergency institutions.

20 Claims, 23 Drawing Sheets

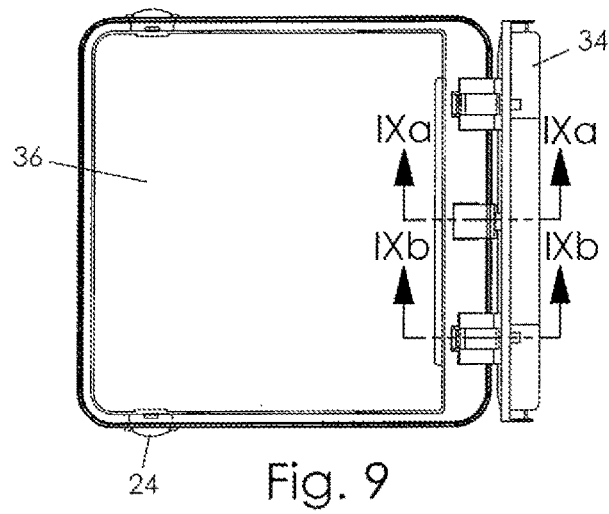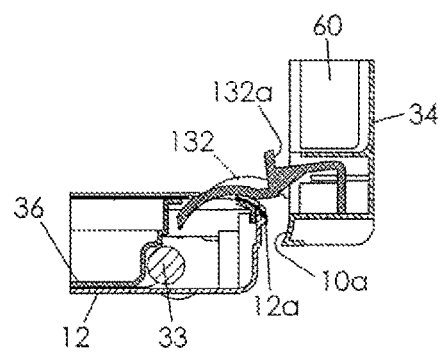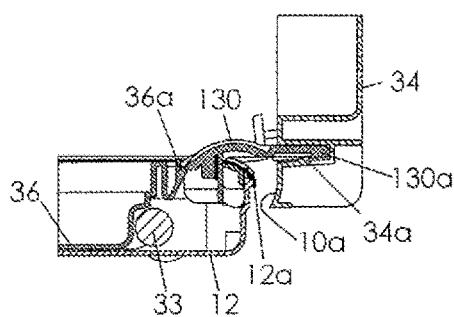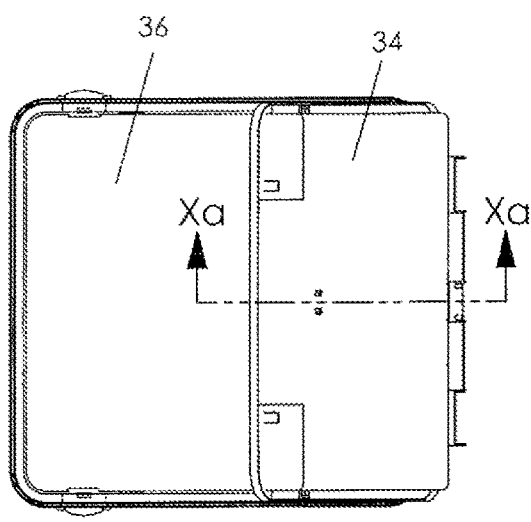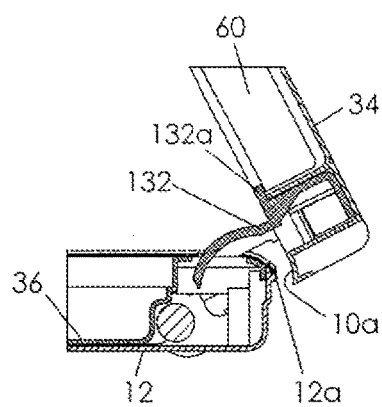

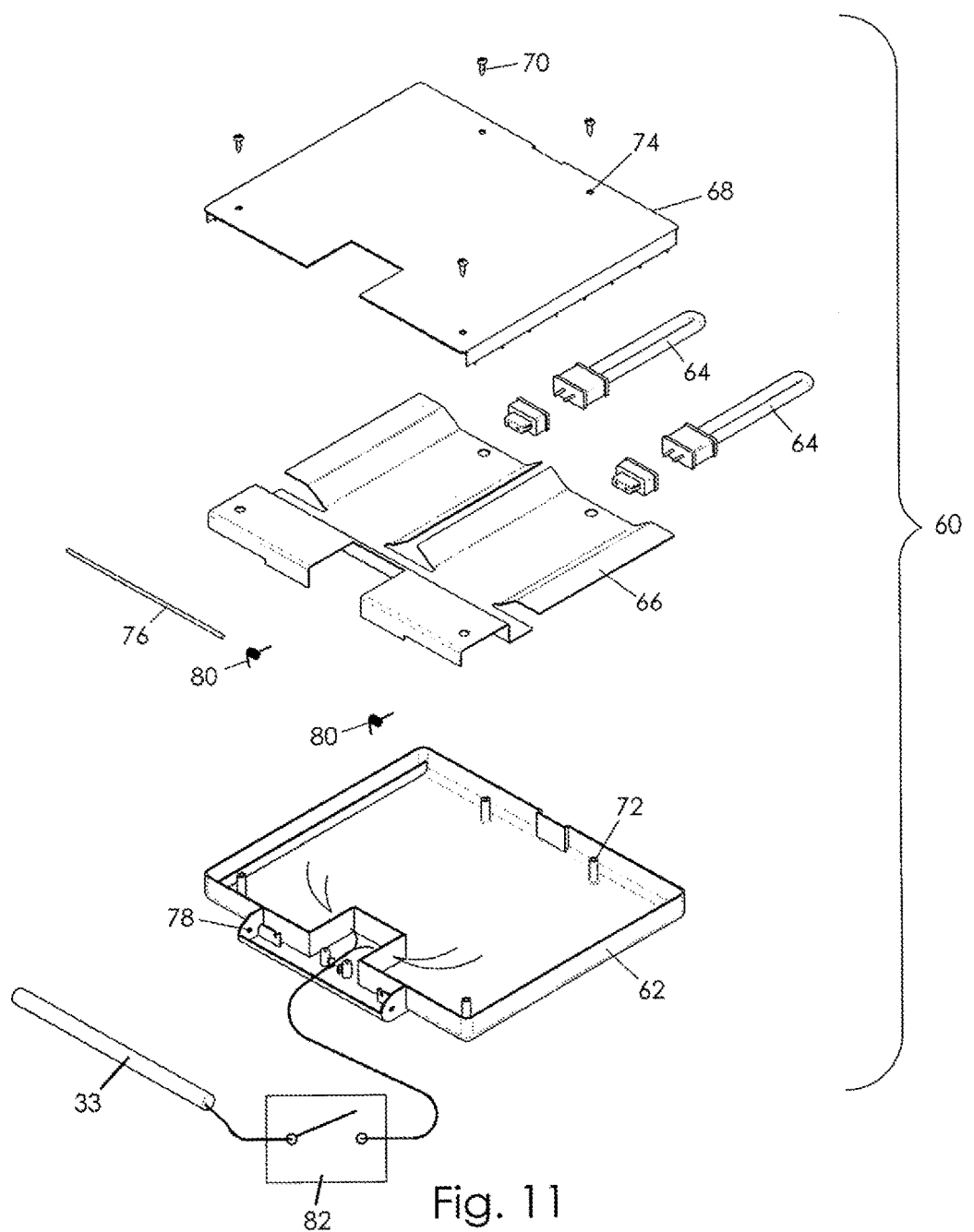

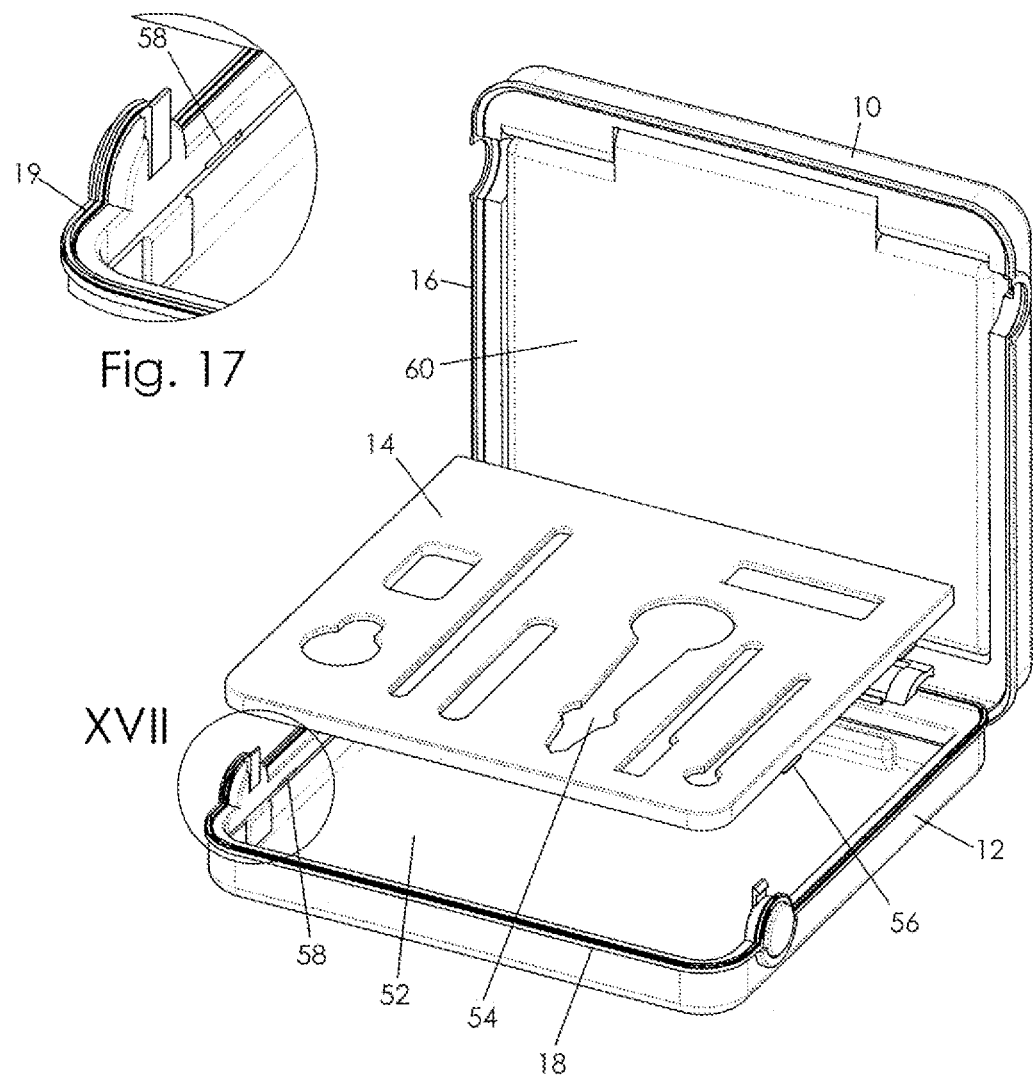

MEDICAL TOOL KIT

This application is a continuation-in-part of pending U.S. patent application Ser. No. 13/228,085, filed Sep. 8, 2011, entitled MEDICAL TOOL KIT, which is incorporated herein by reference.

BACKGROUND OF THE INVENTION

1. Field of the Invention

The invention relates generally to a medical tool case for packaging, storing, and transporting medical instruments and tools. In particular, the invention relates to a medical tool kit capable of providing continuing sterilization of the medical instruments and tools kept inside the storage case, during the normal use of the medical tool kit. More particularly, the invention relates to a medical tool case equipped with a global positioning system (GPS) or other locator signal source that automatically emits a signal upon opening of the case to aid first responders in locating the case's (and by extension, the patient's) location. A further aspect of the invention provides the user with two way communication to the local emergency department by utilizing a microphone and speaker, and display, such as a touch screen liquid crystal display (LCD). More particularly the invention is equipped with access to a library of certified medical procedures as defined by state, regional, and local regulatory agencies. The invention further provides the user with an external light source and robust carrying handle assembly.

2. Description of the Related Art

Various medical procedure kits have been used for packaging, storing, and transporting medical instruments and tools for diagnosis, treatment, and other medical procedures. Typically, medical instruments and tools are sterilized before being packaged in a sterilized storage case. The storage case is then sealed to prevent the sealed medical instruments and tools from contamination.

When using the medical procedure kits during a medical procedure, the user opens the storage case and removes a medical instrument and tool from the storage case as needed in a particular medical procedure. The non-selected medical instruments and tools remain in the storage case until they are need in the medical procedure.

Once the storage case is opened, the medical instruments and tools stored inside the storage case can be subjected to contamination, even when the medical procedure is conducted in an operation room. Such contamination can compromise the sterilization of the medical instruments and tools stored in the medical tool kit.

Further, prudent residents within areas prone to natural disasters, such as a hurricane, tornado, mudslide or earthquake, will include a first aid kit and/or other medical treatment paraphernalia in their disaster preparedness supplies. Nevertheless, in cases of serious injury during a disaster, receiving proper care in a timely manner is dependent upon emergency personnel and other first responders being able to quickly locate the injured.

Thus, it is desirable to provide a sterilizing medical kit, which is capable of maintaining the sterilized condition of the medical instruments and tools stored in the storage case after the storage case is opened during the medical procedure. The medical kit is further equipped with a signaling device, such as a GPS tracking device, which automatically activates upon opening of the kit so as to enable first responders to locate the kit and injured party. Upon locating the injured party, the medical kit provides the user with hands free audio and visual connection between local medical centers, emergency personnel and a certified database of regulated procedure protocols.

SUMMARY OF THE INVENTION

According to an embodiment of the present invention, a medical tool kit includes top and bottom halves. A tray holding medical instruments and tools is arranged in the bottom half and a UV light assembly is arranged in the top half. The top and bottom halves of medical tool kit are sealed in a closed position to maintain a sterile condition of the medical instruments and tools therein. Upon opening the medical tool kit, the UV light assembly directs UV light onto the medical instruments and tools stored inside the medical tool kit to prevent contamination while the instruments and tools are waiting to be used during a medical procedure. The kit may be designed to be procedure-specific with some indicia to indicate the particular use. In one embodiment, the medical tool kit is a disposable kit.

According to another embodiment of the present invention, a medical kit includes a case housing with a first housing part and a second housing part, wherein the first and second housing parts are movable relative to each other between a closed position and an open position, one of the first and second housing parts being configured to hold at least one of a medical instrument, a tool, or a supply. The medical kit further includes a seal sealing an interior of the housing when the first and second housing parts are in the closed position, so that contamination of the at least one of the medical tool, the instrument, or the supply is prevented by the seal, whereby a sterile state of the at least one of the medical instrument, the tool, or the supply is maintained while the case remains in the closed position. The medial kit may further include a light assembly, such as a light emitting diode (LED) assembly arranged on the exterior of the first and/or second housing parts. Furthermore the medical tool kit contains a handle assembly.

In accordance with an aspect of the present invention, a switch may be connected to the internal battery and the external LED assembly located on the exterior of the first and/or second housing parts. When actuated, the configured switch completes the electrical circuit between the internal battery and LED assembly. A UV lamp is arranged in the case housing and is actuatable when the housing is opened from the closed position to maintain the sterile state of the at least one of the medical instrument, the tool, or the supply when the case is in the open position. The medical kit further includes a global positioning system (GPS) tracking device as well as hands free audio and video communication devices.

The medical kit may comprise a lamp assembly connected to one of the first and second housing parts, the UV tamp being part of the lamp assembly. According to a further embodiment, the lamp assembly is pivotally mounted to the one of the first and second housing parts so that the lamp assembly is pivotable from a storage position to an operable position in which the UV radiation is directed onto the at least one of a medical tool, a medical instrument, or a medical supply. The lamp assembly may be held in the storage position against the second housing part in the closed position of the case housing and the lamp assembly may pivot away from the second housing part when the housing is open to the operable position in which the UV radiation from the UV lamp is directed onto the at least one of a medical instrument, a medical tool, or a medical supply. The tamp assembly extends approximately 90 degrees from the second housing part in the operable position.

In another embodiment of the present invention, a medical tool kit includes top and bottom halves. A tray holding medical instruments and tools is arranged in the bottom half and a two way communication assembly is arranged in the top half. Upon opening the medical tool kit, the two way communication devices such as a microphone, speaker, and touch screen enabled liquid crystal display assembly direct communication signals towards the user thereby allowing the user to acquire vital hands free procedure instructions and communication with local medical personnel. Furthermore the two way communication assembly allows the medical kit user to use voice activated commands.

In another embodiment of the present invention, a medical tool kit includes top and bottom halves. A tray holding medical instruments and tools is arranged in the bottom half and tablet assembly is arranged in the top half. The tablet assembly may be comprised of a customized tablet device similar to an Apple Ipad, Microsoft Surface, or Samsung Galaxy and mounting hardware so that the tablet device may become detachable from said top half. The tablet device may contain but is not limited to a two way communication assembly with microphone and speaker, GPS device, battery, touch screen LCD, programmable memory, a central processing unit, and wireless connectivity.

The medical kit may further comprise an LED assembly connected to one of the first and second housing parts. The medical kit further contains a mechanical switch located on the exterior of one of the first or second housing parts of first and second handles. The switch is connected to the battery located on the interior of the medical kit and to the LED assembly. Furthermore, the LED assembly is actuatable while the medical kit remains in the storage position and the handle assembly is in the operation position.

In a further aspect of the present invention, the medical kit may comprise a handle assembly connected to one of the first or second housing parts and associated external switch parts. Further the handle assembly can extend in a direction normal to the medical kit when in use to provide more space for the users hand and actuate power to the switch and LED assembly thereby creating the user control for the LED assembly. When not in use the handle can retract into its respective first or second housing part, thereby minimizing the footprint of the medical kit and cutting off power to the LED assembly and switch.

A switch may be used to control the UV light and be configured to actuate the UV light when the lamp assembly is proximate the operable position.

A second switch may be used to control the external LCD assembly and be configured to actuate the LED assembly when the user applies force.

A battery is connected to the UV light, communication devices, external LED assembly and GPS tracking device for powering the UV light, communication devices, external LED assembly and GPS tracking device. A switch controls the UV light, communication devices, and GPS tracking device and is configured to actuate the UV light, communication devices, and GPS tracking device when the case housing is proximate the open position.

The medical kit may further include an aerosol sprayer containing an antiseptic material. The aerosol sprayer may be automatically actuatable to spray the at least one medical instrument, medical tool, or medical supply when the housing is opened from the closed position. A switch controls the UV light, GPS tracking device, communication device and the aerosol sprayer and is configured to actuate the UV light, GPS tracking device, microphone, speaker, LCD screen and the aerosol sprayer when the case housing is proximate the open position. Furthermore, upon actuation the GPS device transmits time stamped geographical coordinates that may be used to allow a concerned party to become aware that the medical kit has been opened and is in use.

In one embodiment, first and second liners inserted in said first and second housing parts, respectively. In this embodiment, the seal may additionally or alternatively be arranged between said first and second liners. A tray holding the at least one of a medical tool, a medical instrument, and a medical supply is held in one of said first and second liners.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings, wherein like reference characters denote similar elements throughout the several views:

FIG. 9 is a top view of the opened medical tool case of FIG. 8;

FIG. 9A is a cross section view of line A-A through FIG. 9;

FIG. 9B is a cross section view of line B-B through FIG. 9;

FIG. 10 is a top view of the partially closed medical tool case of FIG. 8;

FIG. 10A is a cross section view of line C-C through FIG. 10;

FIG. 11 is an exploded schematic view of a lamp assembly;

FIG. 16 is a perspective view of the medical tool assembly kit showing the attachment of a tool support insert;

FIG. 17 is a perspective view of detail J of FIG. 16;

DETAILED DESCRIPTION OF THE EMBODIMENTS

Figure 1:
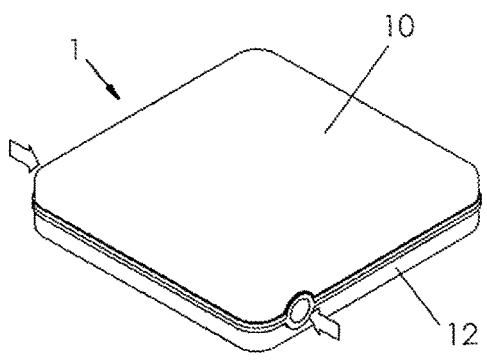
FIG. 1 is a perspective view of an embodiment of a medical tool case formed according to the invention in a closed position.
Figures 2, 2B:
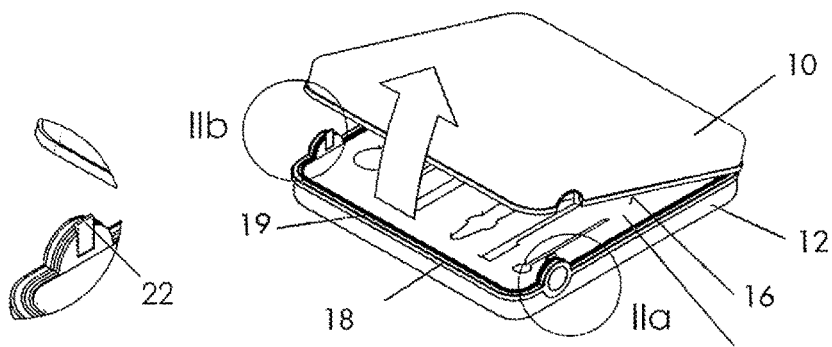
FIG. 2 is a perspective view of the embodiment of the medical tool case of FIG. 1 in an open position.
FIG. 2B shows a detail B of the medical tool case of FIG. 2.

FIGS. 1 and 2 show a medical tool kit 1 according to an embodiment of the present invention in closed and partially opened positions. The medical tool kit 1 generally includes upper and lower casings 10, 12, which can be configured in various forms for storing and retaining various types of medical instruments and tools inside the medical tool kit 1. In one example, the medical tool kit 1 includes a tool support insert 14 to be fit in the lower casing 1 and configured for supporting various types of medical instruments, tools, and supplies. The upper and lower casings 10, 12 can be joined to each other by any of various pivotal joints and hinges, so that the upper and lower casings 10, 12 are movable into the open and closed positions. The detailed configuration of the medical tool kit 1, including the upper and lower casings 10, 12, will be described below.

Figure 2A:
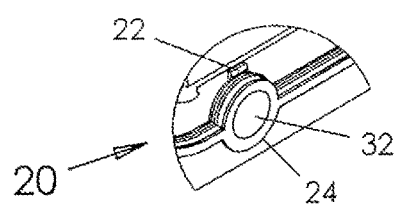
FIG. 2A shows a detail A of the medical tool case of FIG. 2.

The upper and lower casings 10, 12 of the medical tool kit 1 can be closed to seal the medical instruments and tools therein. In one example, the rims 16, 18 of the respective upper and lower casings 10, 12 are formed to seal against each other when the medical tool kit 1 is in a closed position. One or more locking devices 20 (see FIGS. 2A and 2B are provided to secure the upper and lower casings 10, 12 in the closed position. For example, the locking device 20 can include one or more latches 22 formed on one of the upper and lower casings 10, 12 for engaging a complimentary slot structure 38 in the other one of the upper and lower casings 10, 12. Various other types of locking devices can also be employed to secure the upper and lower casings 10, 12 in the closed position.

Figure 1A:
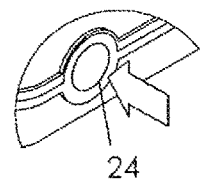
FIG. 1A shows a detail of the medical tool case of FIG. 1.

The upper and lower casings 10, 12 can be opened to an open position to allow access to the medical instruments and tools stored inside the upper and lower casings 10, 12. In one example, each locking device 20 includes a lock release 24 (see FIGS. 1A and 2A) for releasing the latch 22 from a locking position to allow the upper and lower casings 10, 12 to be opened to the open position. Here, the lock release 24 includes a tab or button 32 that can be pressed inward, i.e., toward an interior of the medical case. The tab 32 and latch 22 may be formed as part of the lower casing as shown in FIGS. 1 and 2. Alternatively, the latch and/or tab may comprise a separate component attached to the casing by adhesive, fastener, or any known or hereafter developed connection. A preferred embodiment of latch and tab is described in more detail below.

In the example shown in FIGS. 1 and 2, each of the upper and lower casings 10, 12 has a substantially rectangular shape. Additionally or alternatively, the upper and lower casings 10, 12 can be formed by molding or various other known methods. The upper and lower casings 10, 12 can be formed of various materials suitable for medical usage. For example, metal (such as stainless steel) and plastic materials can be used to form the upper and lower casings 10, 12. In one example, the upper and lower casings 10, 12 can be made of medical grade resins.

The details of the various components of the medical tool kit 1, as well as the process of forming and assembling the medical tool kit 1, are illustrated in FIGS. 3 to 19 and will be described below.

Figure 3:
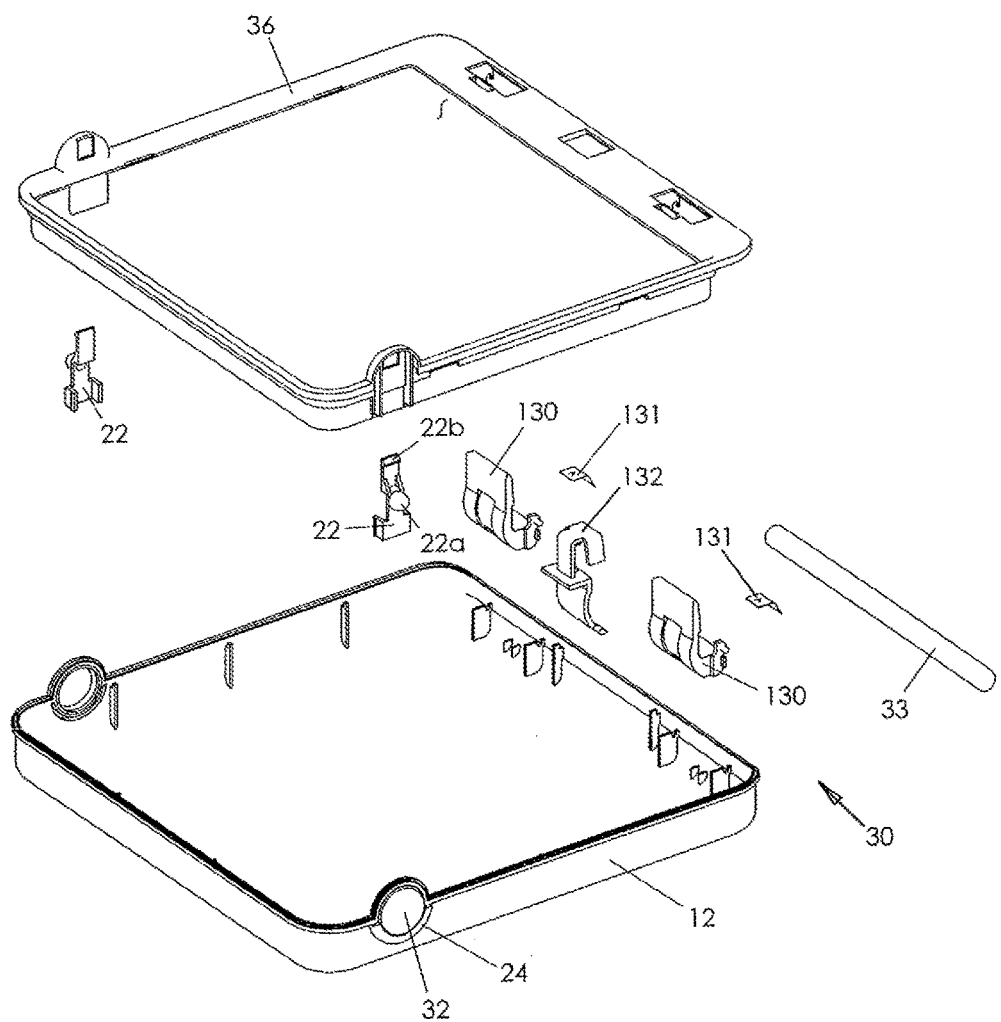
FIG. 3 is an exploded perspective view of the lower casing and bottom liner of the medical tool case of FIG. 1.
Figure 4:
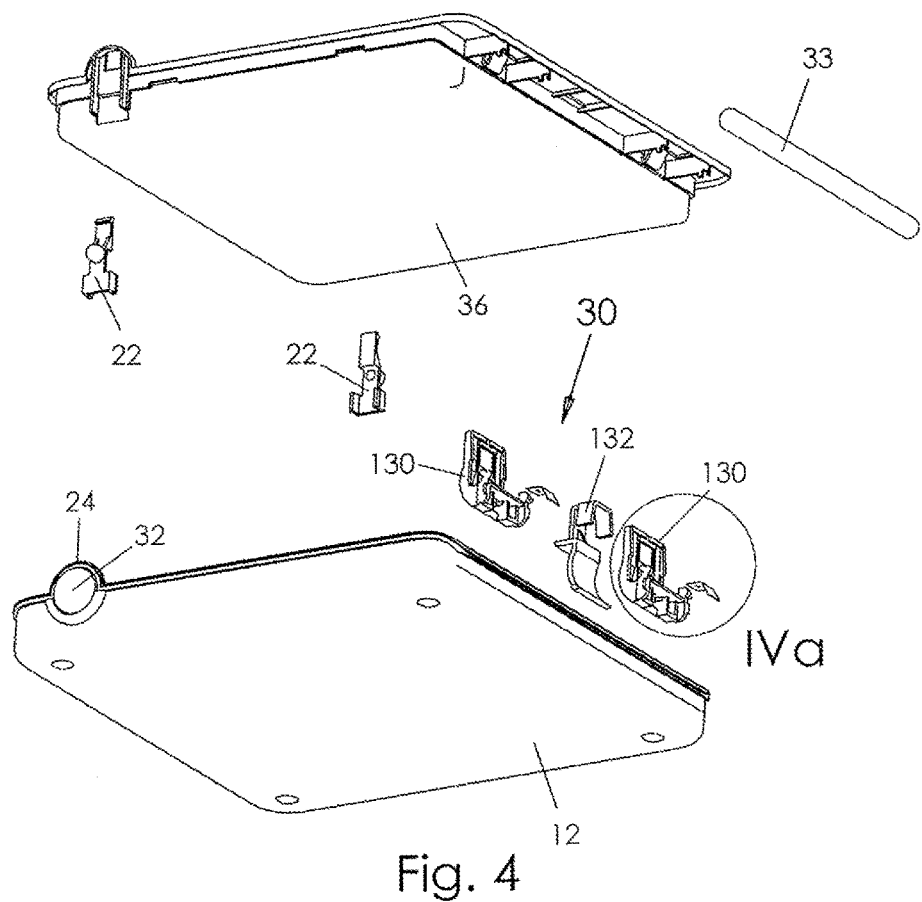
FIG. 4 is an exploded bottom perspective view of the lower casing and bottom liner of the medical tool case of FIG. 1.
Figure 4A:
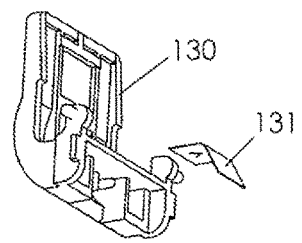
FIG. 4A is an enlarged view of detail A of FIG. 4 showing a hinge piece.
Figure 5:
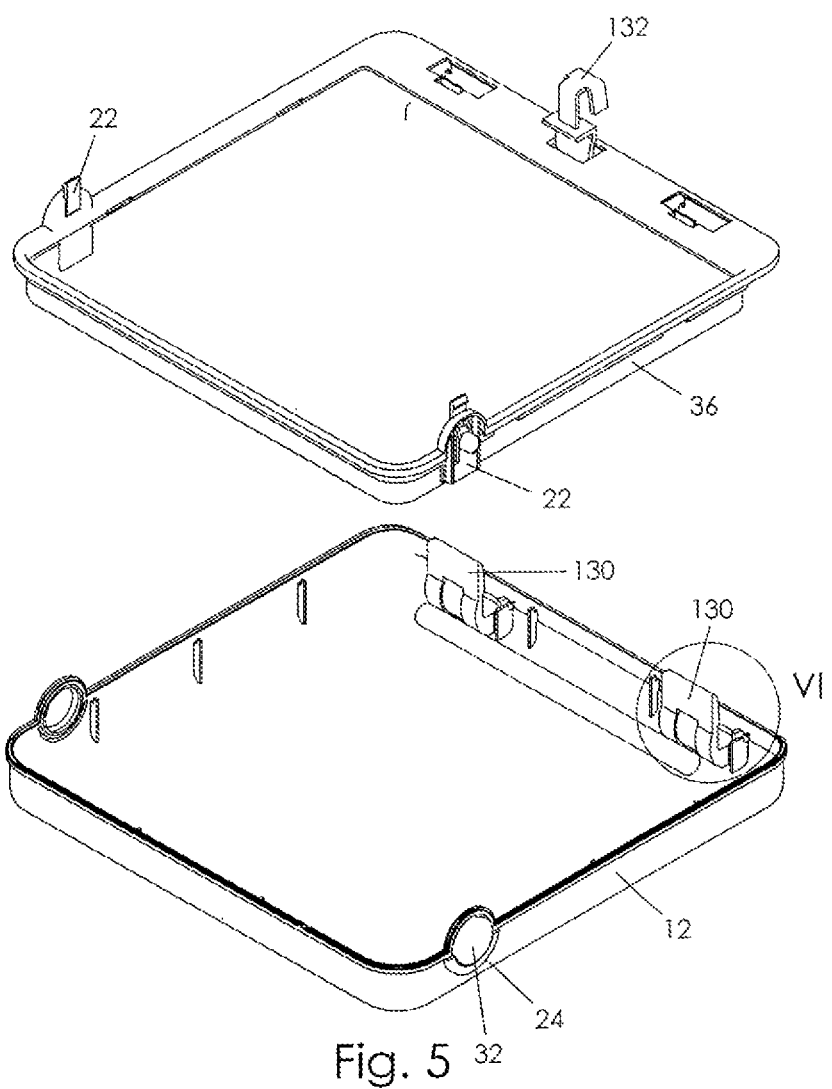
FIG. 5 is a perspective view of the lower casings of the medical tool case of FIG. 1 with the hinges installed.

FIGS. 3-5 show the lower casing 12 with a bottom liner 36. On one example, the bottom liner 36 is closely fit inside and permanently attached to the lower casing 12. Alternatively or additionally, the bottom liner 36 is welded or otherwise connected to the lower casing 12. Although the embodiments depicted include a bottom liner 36 received in lower casing 12 and a top liner 36 received in the upper casing 10, in an alternative embodiment the casings may be molded so that they do not require the liners.

Figure 6:
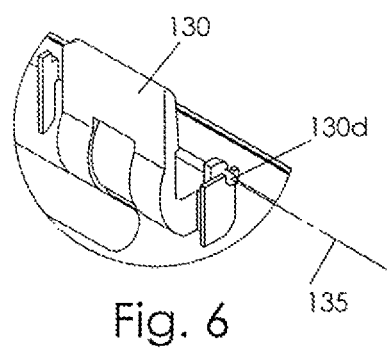
FIG. 6 is a perspective view of an installed hinge piece of the lower casing of FIG. 5.

Referring back to FIGS. 3-5, a hinge 30 is provided to join the upper and lowers casings 10, 12 while allowing the upper and lower casings 10, 12 to pivot between the open and closed positions. In one example shown in FIGS. 3-5, two hinge pieces 130 are pivotally connected to the lower casing 12. FIG. 6 is a detailed view of one of the hinge pieces 130 showing a boss or projection 130d pivotally connected to the lower casing 12. A pivoting axis 135 of the hinge 30 is formed at a location away from the rim of the lower casing 12 so that when the upper and lower casings 10, 12 are in the closed position, the medical tool kit is sealed along the upper and lower rims 16, 18 of the casings 10, 12 by a sealing gasket 19 to prevent the content inside the medical tool kit from being exposed to possible contamination (see FIG. 2). To provide clearance for the opening and closing movement, the portions of the rims 16, 18 behind the pivoting axis 135 of the hinge 30 each have a curve 10a, 12a (see FIGS. 9A, 9B, 10A), that avoids interference between the two parts. Optionally, a spring mechanism, such as spring 131 acting on the hinge piece 130, can be incorporated in the hinge joint 30 to assist in opening the medical tool kit 1 in a known manner.

FIGS. 3-5 also show a battery 33 provided to supply power to one or more UV lamps 64 (see FIG. 11), as is described below. In one example, the battery 33 is installed inside the medical tool kit 1, thereby minimizing exposure of the interior of the medical tool kit 1 through an external electrical contact. In the embodiment shown in FIGS. 3-5, the battery 33 is mounted between the lower casing 12 and the bottom liner 36 proximate the hinge joint 30 by various known or hereafter developed methods and electrically connected to the UV lamps 64. However, the battery may also be arranged at any other suitable location in the medical tool kit 1. In FIGS. 3-5, the battery 33 is located in the lower casing 12 to minimize the weight of the upper casing 10.

As further shown in FIGS. 3-6, the lower casing 12 includes one or more buttons 32, which can be subjected to deformation upon activation of the lock release 24. For example, the release buttons 32 can be formed of a rubber material and co-molded with the lower casing 12. The release buttons 32 are deformable inward by manual pressure to allow the user to activate the lock release 24 located inside the medical tool kit 1 as described in the embodiment below. As one skilled in the art will appreciate, various other materials can be used to form the upper and lower casings 10, 12.

Figure 7:
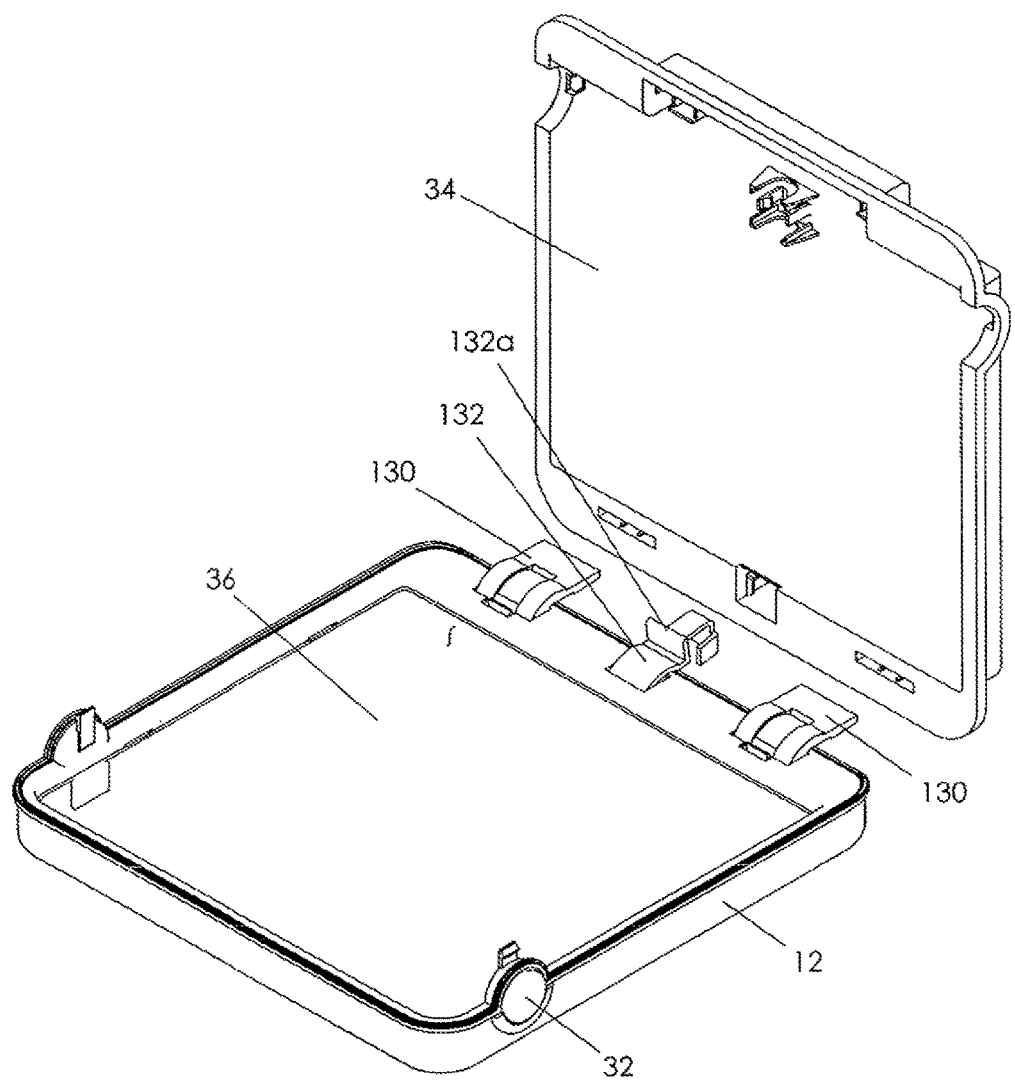
FIG. 7 is a perspective view of the medical tool casing of FIG. 1 showing the insertion of the top liner onto the hinge.
Figure 8:
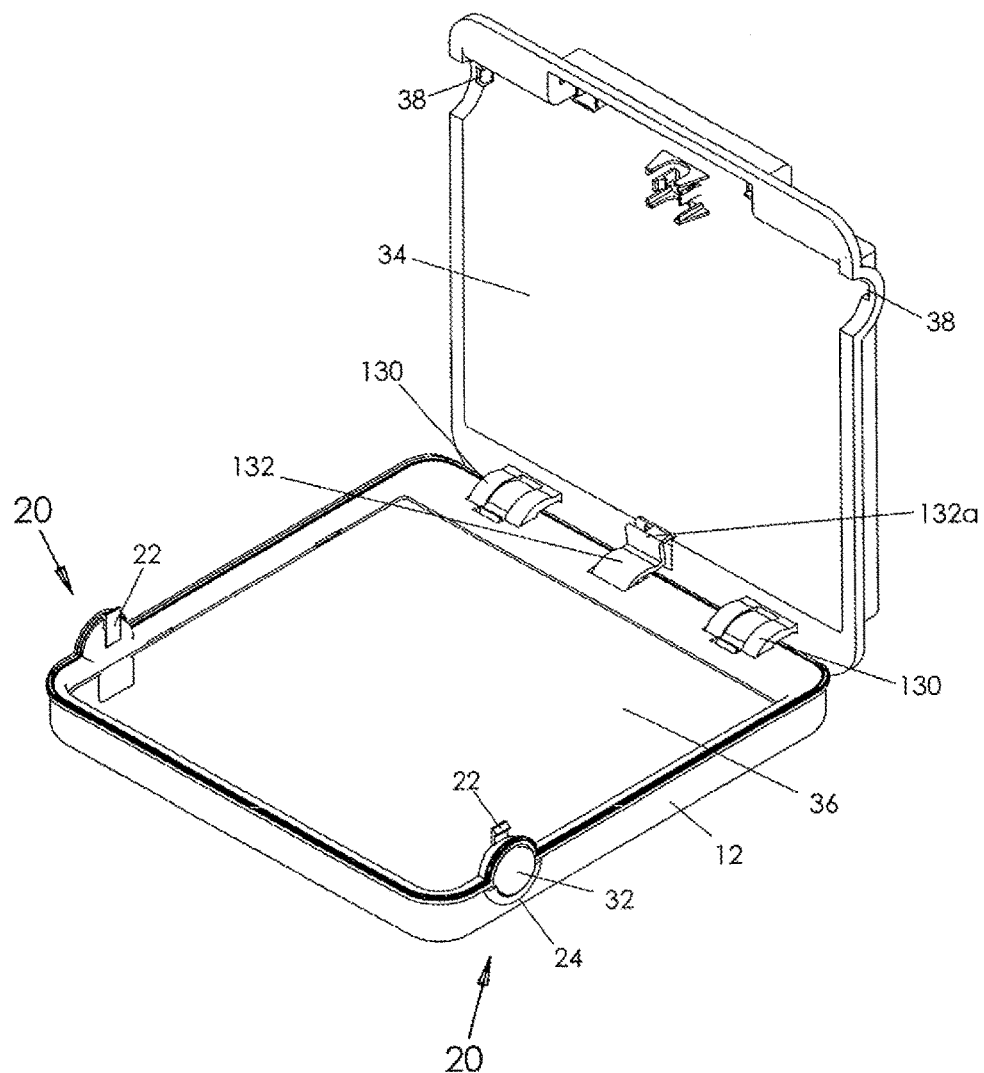
FIG. 8 is a perspective view of the medical tool case of FIG. 1 showing the top liner in the installed state.

In FIGS. 7-8, a top liner 34 is connected to the hinge pieces 130, which are already pivotally mounted in the lower casing 12 and bottom liner 36. Various methods can be used to form the top and bottom liners 34, 36. For example, the top and bottom liners 34, 36 may be injection molded. In a preferred embodiment, the hinge pieces 130 are snap fit into the top liner 34. However, any known or hereafter developed connection between the hinge pieces 130 and the top liner 34 may be used. FIG. 9 shows the connected top liner 36 in the open position and FIG. 9B show cross sections of the respective hinge piece 130 in the open position. FIG. 9B shows an example of a snap fit connection in that resilient portion 34a of top liner 34 holds abutment portion 130a of hinge piece 130. FIG. 9B shows a cross section of a center latch piece 132, which will be described in more detail below. In addition, a resilient abutment 36a on the bottom liner 36 facilitates holding the top liner 34 in the open position. FIG. 10 shows the top liner 34 in a partially closed position and FIG. 10A shows a cross section of center latch piece 132 in that position. Although two hinge pieces 130 are shown, one or more hinge pieces may alternatively be used. For example, a single one of the hinge pieces 130 may be used at the location of the central hinge piece 132 in an embodiment requiring only one hinge piece.

In the depicted example, the top and bottom liners 34, 36 are formed with one or more of the locking devices 20. In the example shown in FIGS. 7-8, a pair of locking devices 20 are located on the lateral sides of the lower liner 36. The locking devices 20 are adapted to be released upon simultaneous operation of the lock release 24, thereby preventing unintended opening of the medical tool kit 1 during handling. The locking devices 20 can be in various forms such as, for example, a latch 22, formed on the lower liner 36. The latch 22 engages a complimentary structure, such as the slot 38, formed in the upper liner 34. When the medical tool kit 1 is in the closed position, the latch 22 on the lower liner 36 is inserted in the slot 38 on the upper liner 34, thereby locking the upper and lower casings 10, 12 in the closed position, Instead of being arranged on liners 34, 36, the latch 22 and slot 38 may be arranged on the upper and lower casings 10, 12 or another element that is attached to the upper and lower casings 10, 12. If the upper liner is not present, the latch is received in a slot 38 in the upper casing 10. Likewise, if the lower liner is not present, the latch 22 is connected directly to the lower casing 12.

The latch 22 for each locking device 24 is a plastic or metal piece that is inserted into the bottom liner 36 at or proximate the tab 32. As shown in FIGS. 3-4, the latch includes a boss 22a interacting with the button 32 and a latch piece 22b that provides the locking function with the slot 38. In a further embodiment, the latch 22 may be made as an integral part of one of the top and bottom liners 34, 36 instead of as a separate piece. In that embodiment, the top and bottom liners 34, 36 themselves may include respective sealing surfaces for hermetically sealing the top and bottom liners 34, 36. The sealing surfaces include the rims of the respective top and bottom liners 34, 36. In one example, the rims 44, 46 of the respective top and bottom liners 34, 36 overlap and hermetically seal against each other, when the medical tool kit 1 is in the closed position. In another example, the rim on the lower liner 36 can be formed with a rubber gasket to seal against the rim on the top line 34. For example, the rubber gasket 48 can be co-molded with the lower liner 36. As a result, the medical instruments and tools inside the medical tool kit 1 are protected against contamination. The seal created by the sealing surfaces can be used as an alternative to or in addition to the sealing of the upper and lower casings.

FIGS. 11-14 shows a lamp assembly 60 for keeping the medical instruments, tools, and supplies in the medical tool kit 1 sterile after the tool case 1 has been opened, using UV light. The LTV light prevents contamination of the medical instruments and tools stored inside the medical tool kit 1 while they are waiting to be used during a medical procedure. For example, the lamp assembly 60 is supported in the upper chamber 38 formed in the upper liner 34. In an alternative embodiment without the upper liner 34, the lamp assembly 60 is mounted directly in the upper casing 10. The lamp assembly 60 includes a lamp assembly cover 62, in which one or more UV lamps 64 are supported. The UV lamps 64 are electrically connected to and thus powered by the battery 33.

In one example, one or more switches 82 are provided and connected between the UV lamps 64 and the battery 33 to control the operation of the UV lamps 64. For example, the switch 82 can be manually turned on when the medical tool kit 1 is in normal use. In another example, the switch 82 is a position switch that is closed to connect the UV lamps 64 to the battery 33 for power supply when the lamp assembly 60 is opened to its operation position as is shown in FIGS. 21D and 21E.

As FIGS. 11-14 show, the lamp assembly 60 has a reflector 66 provided to direct the UV radiation generated by the UV tamps 64 during the operation of the lamp assembly 60. In one example, the reflector 66 is positioned between the lamp assembly cover 62 and the UV lamps 64. If desired, a clear panel 68 can be used to cover the UV lamps 64 for protection.

The various components of the lamp assembly 60 are assembled to form a unitary assembly 60. For example, the lamp assembly cover 62, the reflector 66, and the clear panel 68 are mounted to one another through connecting pins 70 and corresponding connecting holes 72, 74, or other know methods. In one example, a plurality of connecting pins 70 are formed on the lamp assembly cover 62 and pass through connecting holes 72, 74 formed on the reflector 66 and the clear panel 68. The resulting lamp assembly 60 has a substantially rectangular shape and is received in the upper liner 34.

Figure 12:
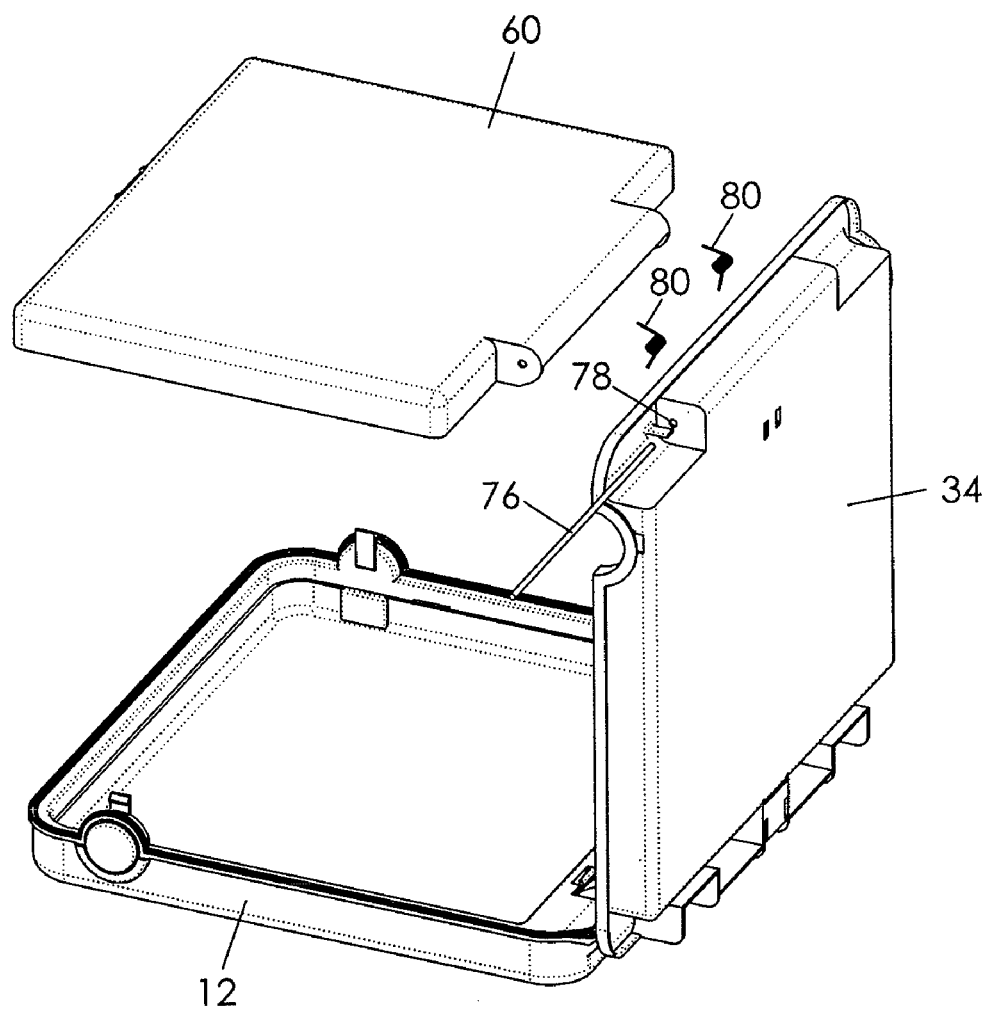
FIG. 12 is a perspective view of the medical tool case of FIG. 1 showing attachment of the lamp assembly.
Figure 14:
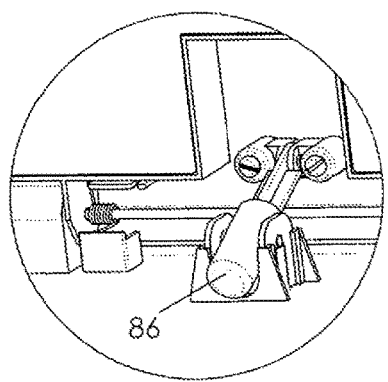
FIG. 14 is an enlarged view of detail B of FIG. 13 showing a dashpot used to connect the lamp assembly to the top liner.
Figure 13:
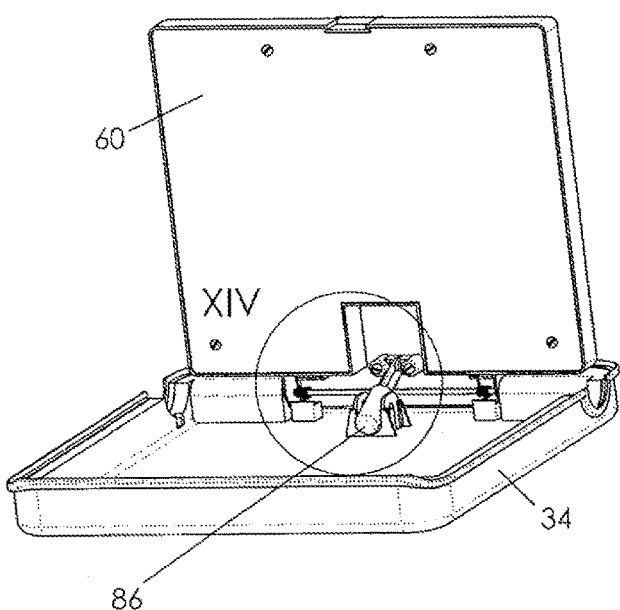
FIG. 13 is a perspective view of the lamp assembly showing the attachment to the front of the top liner.
Figure 15:
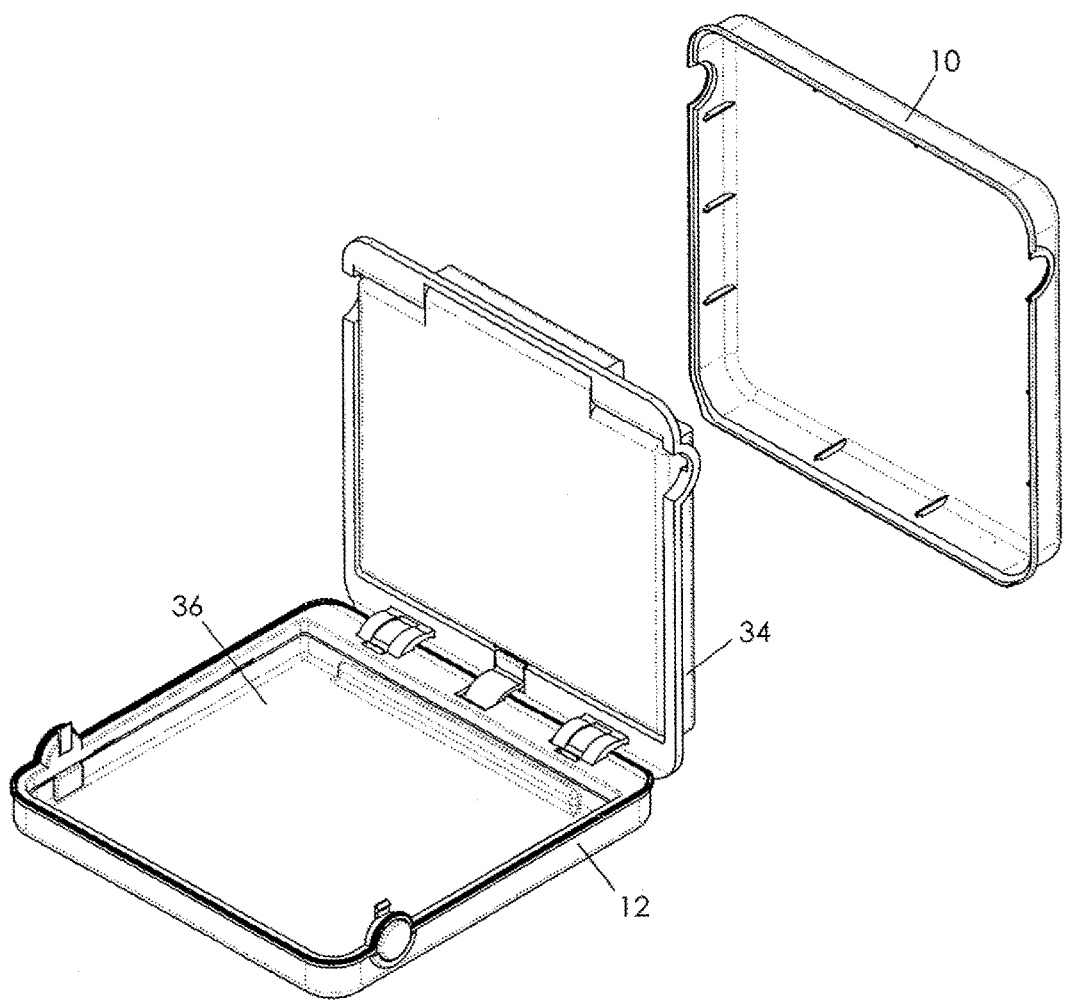
FIG. 15 is a perspective view of the medical tool assembly kit showing the attachment of the upper casing to the top liner.

In one embodiment, the lamp assembly 60 is pivotably attached to the upper liner 34. A hinge pin 76 is provided to attach the lamp assembly 60 to the upper liner 34. As FIGS. 11-12 show, the upper liner 34 is formed with receiving holes 78 to accommodate the hinge pin 76. In another example, a spring loaded hinge having a spring 80 connected, for example, between the upper liner 34 and the lamp assembly 60, is provided to attach the lamp assembly 60 to the upper liner 34. The spring loaded hinge assists the opening of the lamp assembly 60. To slow the deployment of the lamp assembly 60 from the stored position to the opened position, a dashpot 86 is arranged between the lamp assembly 60 and the top liner 34 and/or upper casing 10 (see FIG. 14). The center latch piece 132 holds the lamp assembly 60 in the top liner 34 until the upper casing 10 is opened to a predetermined extent that provides clearance for the lamp assembly 60 pivot to the open position. As shown in FIGS. 9A and 10A, the center latch piece 132 includes a stop 132a which holds the lamp assembly in the top liner 34 until the upper casing 10 is near the fully open position. FIG. 10A shows that the lamp assembly is held in place and FIG. 9A shows that that the lamp assembly is free to pivot outward.

Although the lamp assembly 60 is shown as being pivotable, the lamp assembly may alternatively be stationarily mounted on the upper liner 34 or upper casing 10 such that the UV radiation is directed onto the medical instruments, tools or supplies when the upper casing is in the open position.

Figure 18:
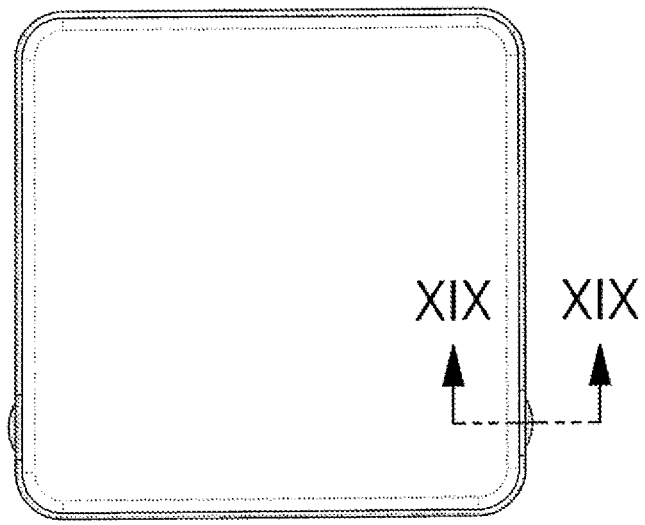
FIG. 18 is a top view of the complete medical tool kit assembly.
Figure 19:
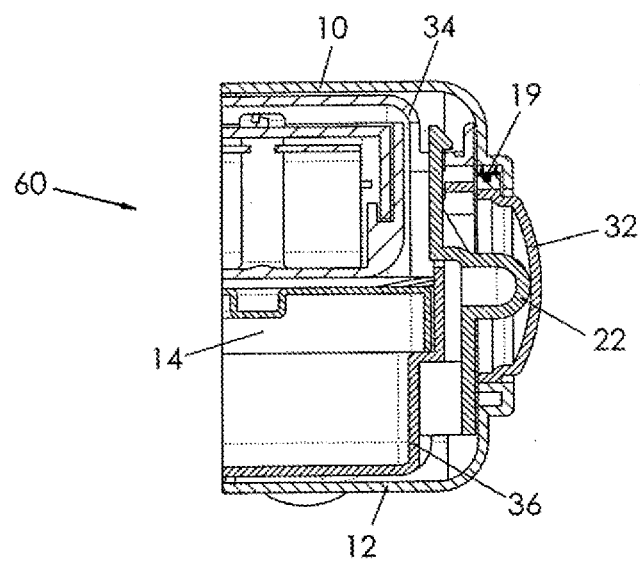
FIG. 19 is a sectional view through line G-G of FIG. 18.

FIGS. 16-17 illustrate further details of the seal between the upper and lower casing. The upper and lower casing 10, 12 are formed with respective upper and lower rims 16, 18. A sealing gasket 19 between the upper and lower rims 16, 18 seals the upper and lower casings 10, 12 when the medical tool kit 1 is in the closed position. The sealing gasket 19 prevents dust, moisture, and/or bacteria from entering the closed medical tool kit 1 or otherwise contaminating the contents sealed in the medical tool kit 1. FIGS. 18-19 show the positions of the upper and lower casings 10, 12 and the top and bottom liners 34, 36, as well as the sealing gasket 19, when the medical tool kit 1 is in the fully closed position.

FIG. 16 also shows the tool support insert 14, i.e., a tray, formed to retain various types of medical instruments and tools (not shown). In the example shown in FIG. 16, the tool support insert 14 has a rectangular plate shape and be received inside the lower chamber 52 formed by the lower liner 36. In an alternative embodiment, the lower liner 36 is not present and the tool support insert 14 is mounted directly into the lower casing 12. The tool support insert 14 is formed with a plurality of tool wells 54 for accommodating portions of medical instruments, tools, and supplies to retain the same in place inside the medical tool kit 1. As is shown in FIG. 16 the tool wells 54 have various shapes in order to receive and retain different types of medical instruments, tools, and supplies.

The tool support insert 14 is removably fitted inside the lower chamber 52 formed by the lower liner 36. In one example, the tool support insert 14 has one or more locking tabs 56 to be removably inserted in corresponding slots 58 formed in the lower liner 36. For example, the locking tabs 56 and the corresponding slots 58 engage with each other by a snapping locking action. Various other locking elements can be provided to retain the tool support insert 14 in place inside the lower chamber in the lower liner 36. As an alternative, the tool support insert 14 may be placed directly in the lower casing 10.

The tool support insert 14 can be formed by various methods and of various materials. In one example, the tool support insert 14 is formed by molding a plastic material, such as a thermoplastic material.

The different medical instruments, tools, and/or supplies stored in the medical tool kit 1 can be used in a particular given medical procedure including a diagnosis or treatment procedure. In one example, the medical tool kit 1 can include a predetermined indicia to indicate the purpose for the medical instruments and tools stored in the medical tool kit 1. In addition, or alternatively, the medical tool kit may be personalized for a specific doctor. The medical tool kit 1 can be color coded to indicate the particular procedure or purpose of the medical instruments, tools, and/or supplies therein. The instruments and tools may comprise, for example, but not limited to, knives, cutting tools, and clamps. The supplies may comprise, for example, but not limited to, bandages, gauze, antiseptic.

In one embodiment, the medical tool kit 1 is a disposable sterile medical tool kit that provides a sterile environment for storing and transporting sterile disposable medical instruments, tools, and/or supplies. In this particular embodiment, the medical instruments, tools, and/or supplies and the medical tool kit 1 are sterilized, assembled and sealed at a sterile facility. The sterile medical tool kits then remain in the sterile environment within the case 1 until they are opened.

As mentioned above, procedure-specific disposable medical kits may be assembled for particular procedures, such as knee surgeries or shoulder surgeries. Alternatively, the sterile medial tool kit could include generic first aid instruments, tools, and/or supplies, such as, for example for a particular user. The medical tool kit may comprise a disposable one-time use kit, in which the disposable sterile medical tool kits are opened when required and then disposed of after use. This allows the medical instruments, tools, and/or supplies themselves to be made of inexpensive materials, such as plastics. In addition, it obviates the costly re-sterilization procedure, which is typically required for medical instruments and tools.

Figure 21A:
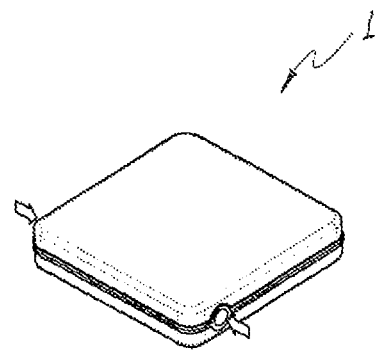
FIGS. 21A to 21E shows the medical tool kit in normal use, in which the medical tool kit is opened from a closed position, while the sterilizing UV light is opened from a closed position to an operating position.
Figure 21B:
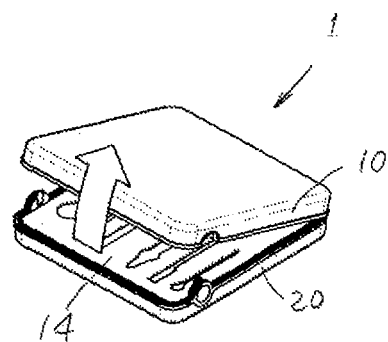
Figure 21C:
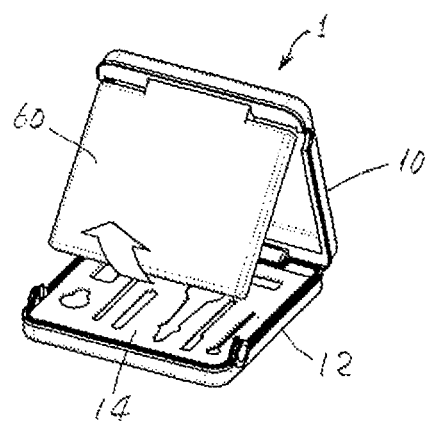
Figure 21D:
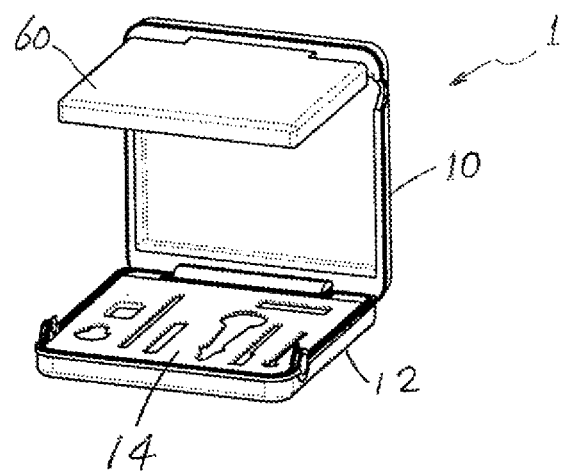
Figure 21E:
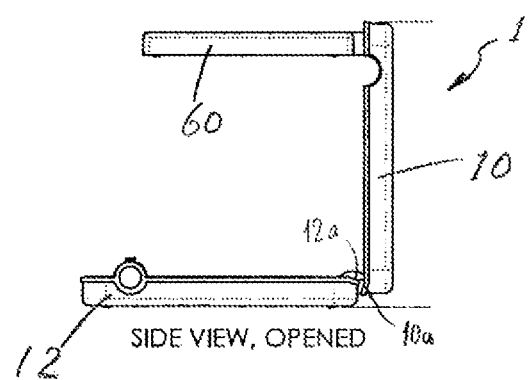

FIGS. 21A to 21E shows the operation of the medical tool kit 1 in a medical procedure. When using the medical tool kit 1, the user first unlocks the medical tool kit 1. In an example shown in FIG. 21A, the user can press the release covers 24 located on the lateral sides of the medical tool kit 1 to release the latches 22. Once the medical tool kit is unlocked, the upper and lower casings 10, 12 can be opened toward the open position, as is shown in FIG. 21B. The opening step can be carried either automatically through the assist of various electrical and/or mechanical mechanism or manually by the user. In one example, the spring mechanism 131 incorporated in the hinge joint 30 assists in at least partially opening the upper and lower casings 10, 12 when the latches 22 are unlocked.

During the process of opening the medical tool kit 1, the lamp assembly 60 is pivoted into its operation position. In one example shown in FIG. 21C, when the upper and lower casings 10, 12 are opened to about 70° or more, the lamp assembly 60 pivots open to its operation position. In an example, the opening operation of the tamp assembly 60 is assisted by a spring mechanism in a spring loaded hinge as described above.

Additionally or alternatively, the UV lamps 64 can be turned on when the lamp assembly 60 is being opened to its operation position. In one example, the user can manually turn on a light switch connecting the ITV lamps 64 to the battery 33. In another example, the UV lamps 64 can be automatically turned on through the operation of an appropriate electrical control circuit. For example, the UV lamps 64 are turned on when the lamp assembly 60 is opened to its operation position as is shown in FIGS. 21D and 21E.

When the medical tool kit 1 is fully opened as is shown in FIGS. 21D and 21E, the upper and lower casings 10, 12 are substantially perpendicular to each other to allow easy access to the medical instruments and tools inside the medical tool kit 1. Additionally or alternatively, the lamp assembly 60 is oriented substantially parallel to the tool support insert 14 to allow UV light to illuminate the medical instruments and tools retained on the tool support insert 14. The illumination can reduce the possibility of microbial contamination after the medical tool kit 1 is opened during normal use in a medical procedure.

In one embodiment, the lamp assembly 60 includes a switch 82, which actuates the UV lamps 64 when the lamp assembly 60 is moved to the operation position (see FIG. 11). The switch may be a mechanical switch that senses the position of the lamp assembly. In a further embodiment, the switch 82 may comprise an optical or light-sensitive switch that actuates the UV lamp 64 when the case is opened and the switch senses light. In embodiments in which the lamp assembly 60 does not move between a storage and operation position, the switch may alternatively be a manual switch.

Figure 20:
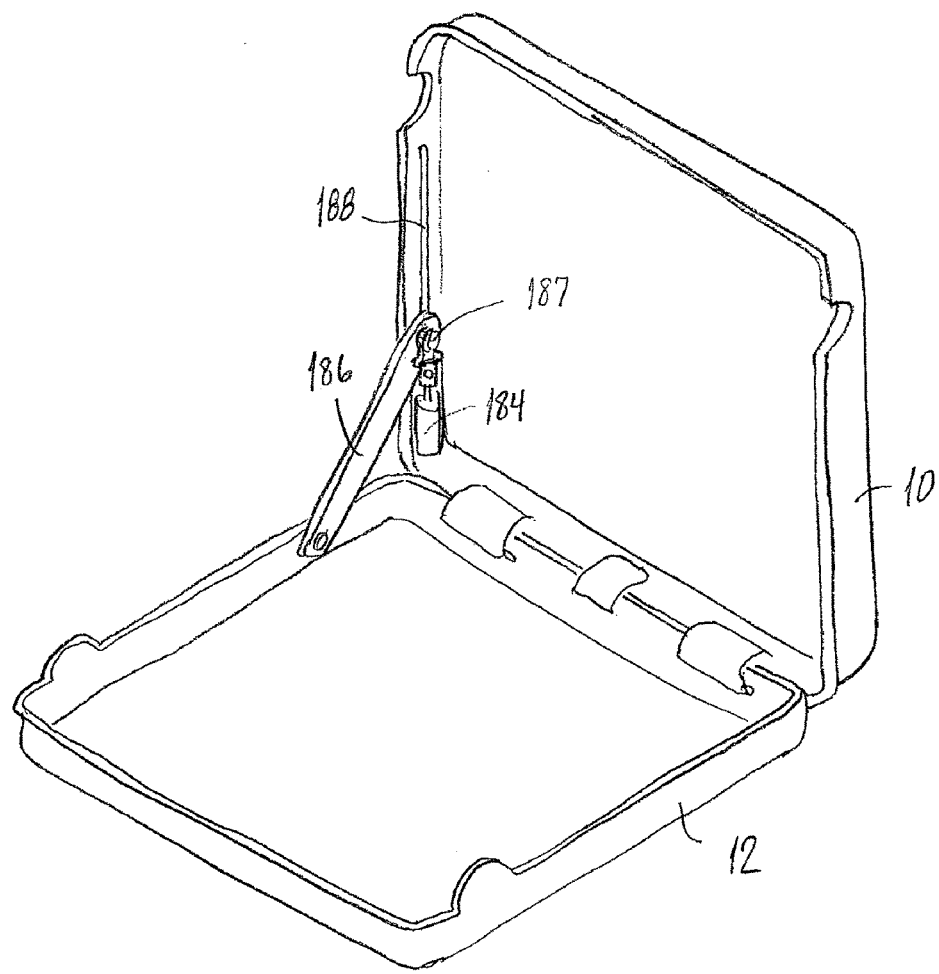
FIG. 20 is a perspective view of an embodiment of the medical tool assembly according to the present invention with an aerosol spray.

Furthermore, the medical tool kit 1 may incorporate an aerosol sprayer 184 containing an antiseptic. In one embodiment, the aerosol sprayer 184 may simply be available as one of the supplies for use by a user. In a further embodiment, the sprayer may be actuated upon opening the case or when the lamp assembly 60 is in the operation position. The aerosol sprayer may be actuated mechanically or electrically using the same or a different switch for actuating the UV light using any known or hereafter developed method. In a specific embodiment shown in FIG. 20, the aerosol sprayer 184 is mounted in the upper casing 10. Alternatively, the aerosol sprayer could be mounted in the upper liner 34. An arm 186 has one end pivotally connected at a sidewall of the lower casing 12. An opposing end of the arm is pivotally connected to a sliding member 187 that is mounted in a rail or guide 188 in the upper casing 10. As the casings 10, 12 are opened, the sliding member 187 slides on the rail or guide 188 toward the aerosol sprayer 184 and actuates the sprayer 184 when the casings 10, 12 reach the open position. The mechanical actuation occurs by interaction between the sliding member 187 (or a part connected thereto) and a valve of the aerosol sprayer.

In one embodiment, the medical kits of the present invention are designed for a one-time field use. In that case, the antiseptic can be continuously sprayed because it is only required for the one use. However, if the case is to be reused, then the antiseptic and the UV light can be intermittently actuated to save the battery and/or aerosol spray for future use.

Figure 22:
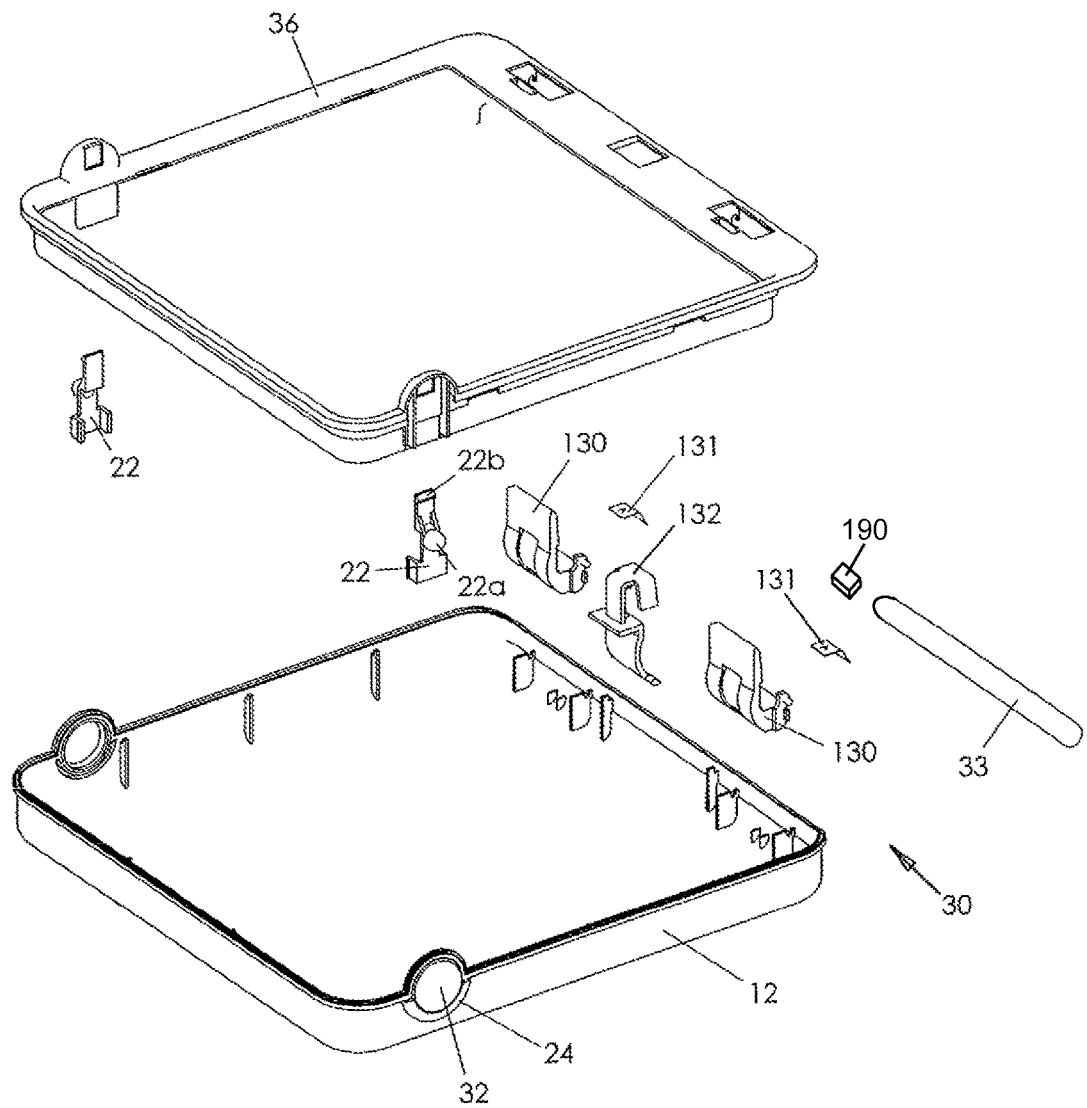
FIG. 22 is an exploded perspective view of an embodiment of the medical tool assembly according to the present invention with a global positioning tracker.
Figure 23:
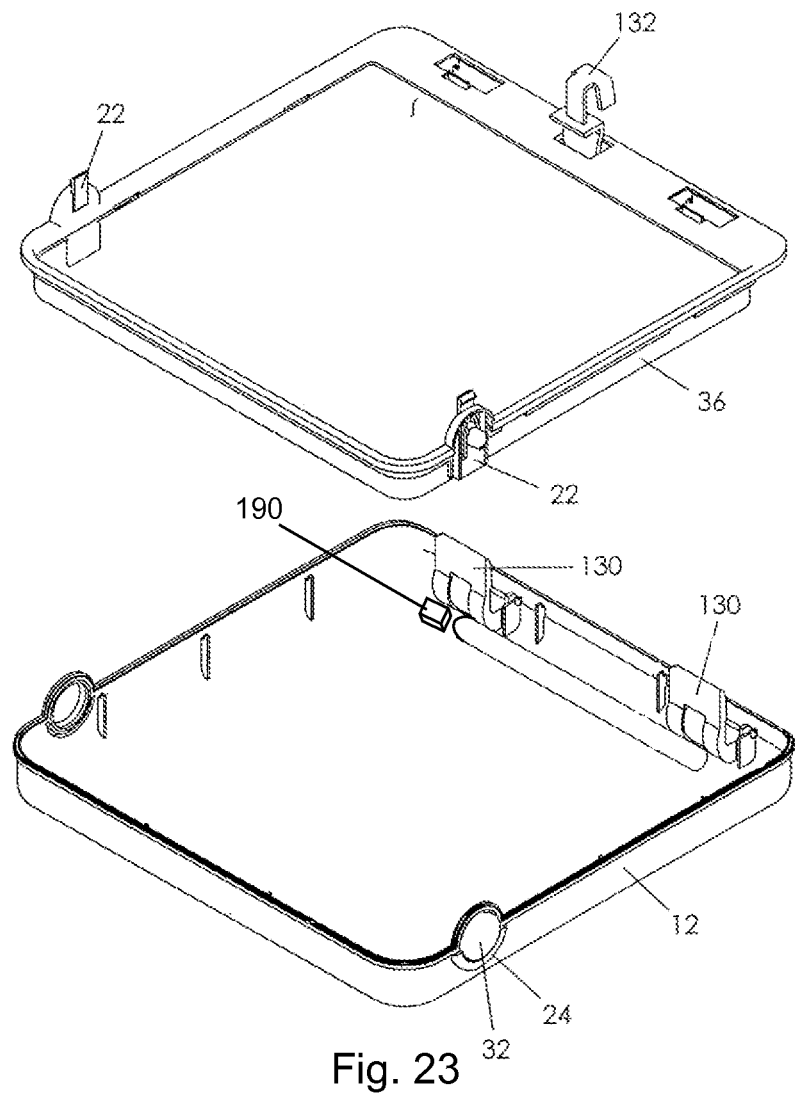
FIG. 23 is a perspective view of the lower casings of the medical tool case of FIG. 22 with the hinges installed.

In accordance with the present invention, medical tool kit 1 may further incorporate a GPS tracking device or other position signaling device 190 as shown in FIGS. 22 and 23. GPS device 190 may be secured within lower casing 12 proximate battery 33 and is actuatable by a switch, such as switch 82 described above. GPS device 190 is in an unpowered state (i.e. not transmitting) when upper casing 10 is secured to lower casing 12 in a closed position. Upon opening the casing, such as during a medical emergency, the switch is closed thereby allowing battery 33 to supply electrical power to GPS tracking device 190 so as to cause the GPS device to broadcast the kit's location. In this manner, remote first responders or other medical personnel may quickly locate the kit (and presumably the injured party). Any suitable switch may be employed, such as a mechanical switch or an optical or light sensitive switch. Additional switches may include for instance, and without necessarily limited the present invention thereto, a magnetically actuated switching device such as a Hall Effect sensor or reed switch in operational configuration with latch 22 and lock release 24 (as shown in FIG. 2A) or latch 22 and slot 38 (as shown in FIG. 8). Similarly, one or more of hinges 130, 132 may include a magnetic switch or other suitable mechanical switch such that pivoting upper casing 10 away from lower casing 12 results in power being supplied to the GPS tracking device 190. GPS tracking device 190 may emit a continuous signal or may, for sake of prolonging battery life, emit a signal intermittently.

Figure 24A:
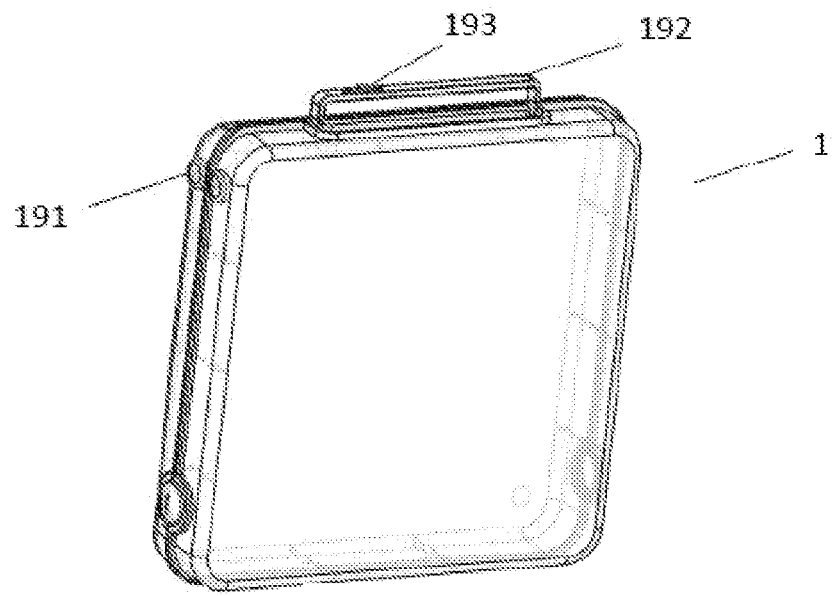
FIG. 24A to 24C are perspective and top views displaying an embodiment of the medical kit with the external LED assembly, handle assembly and switch in the operational position.
Figure 24B:
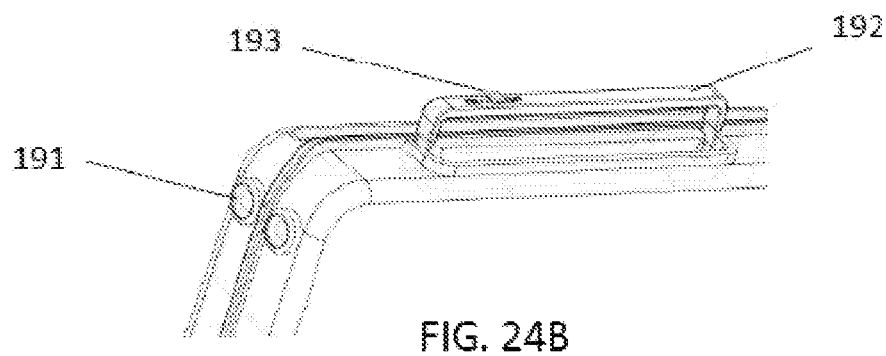
Figure 24C:
Figure 25A:
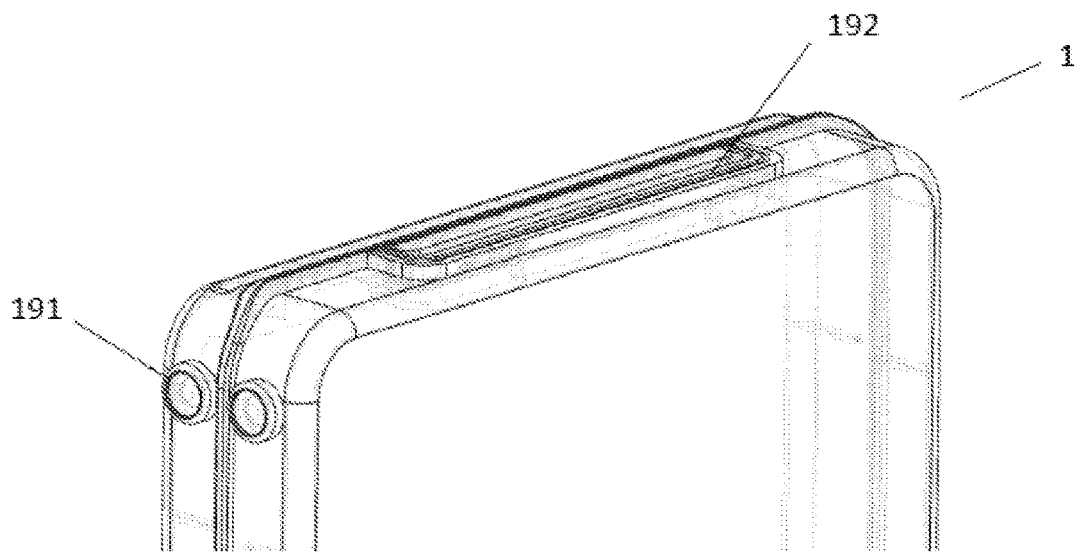
FIGS. 25A and 25B are perspective and top views displaying an embodiment of the medical kit with external LED assembly, handle assembly and external switch in the storage position.
Figure 25B:
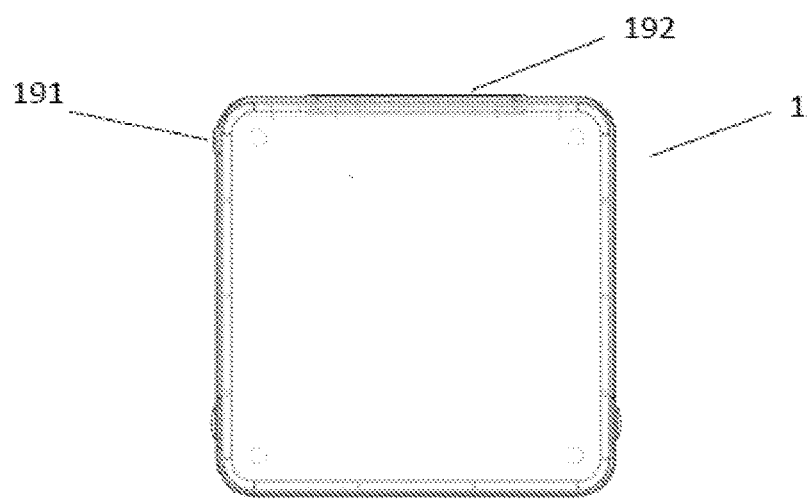

In accordance with the present invention, medical tool kit 1 may further include an external tight assembly, such as light emitting diode (LED) assembly 191, and handle assembly 192 with external switch 193 as shown in FIGS. 24 and 25, LED assembly 191 may be mounted to one or both of upper and lower casings 10, 12 and is connected to battery 33, to supply power for the LED assembly 191, and to an external switch 193. The external switch 193 is capable of completing the electrical circuit containing the LED assembly 191, battery 33 and sufficient electrical resistance. In one embodiment the handle assembly 192 can be in a storage position that reduces the overall footprint of the medical kit 1 as shown in FIG. 25B and the operation position in FIG. 24C.

Figure 26A:
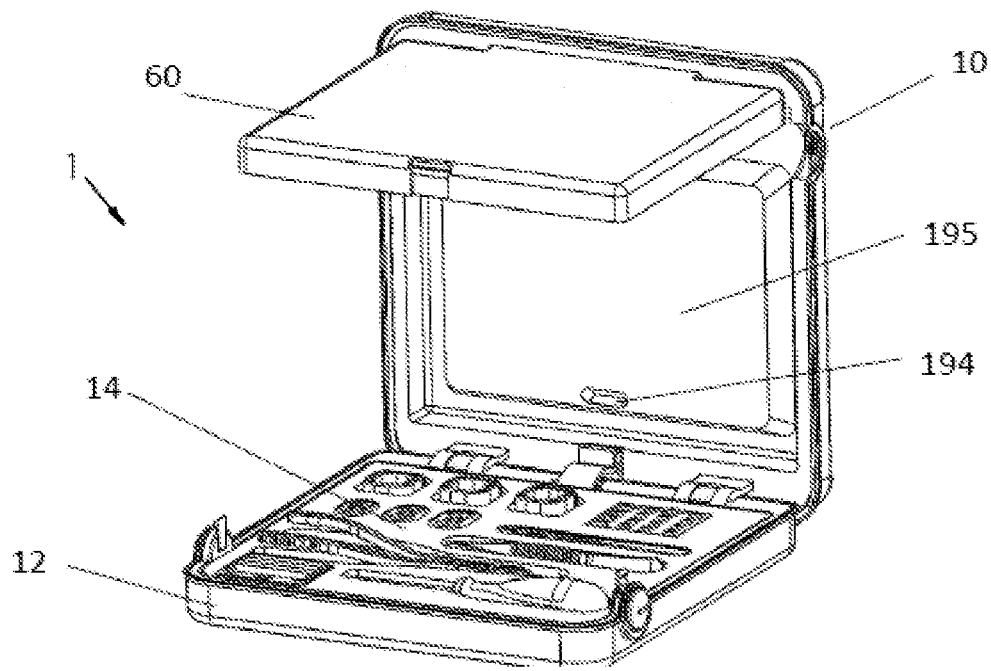
FIGS. 26A and 26B are perspective and front views of an embodiment on the medical tool kit according to the present invention with a two way communication assembly comprised of a microphone, speaker, and display.
Figure 26B:
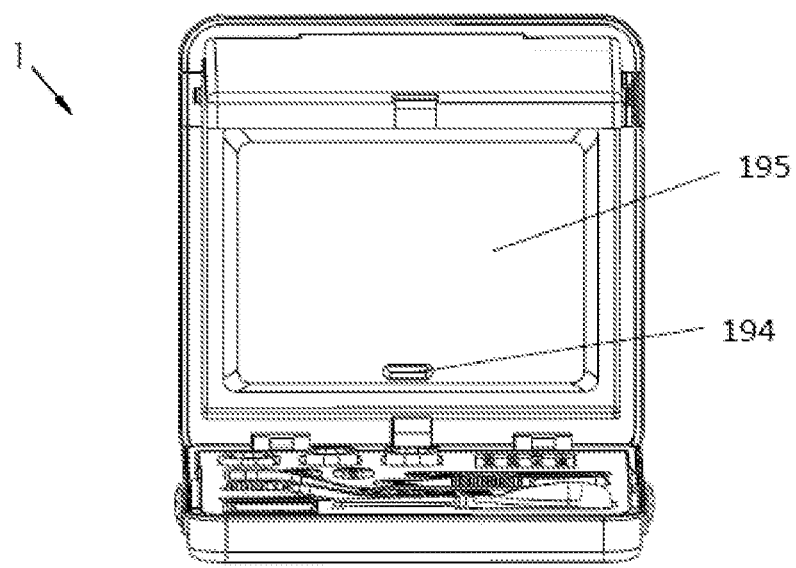

Turning now to FIGS. 26A and 26B, in accordance with the present invention, medical tool kit 1 may further comprise a two way communication assembly capable of connecting to local emergency personnel. In one aspect of the present invention, the two way communication assembly comprises a microphone speaker assembly 194 and a display 195, such as a touch screen liquid crystal display (LED). Microphone speaker assembly 194 and display 195 may be configured to establish wireless communication with remove emergency personnel, such as through Wi-Fi, Bluetooth or other wireless protocol. The microphone speaker assembly 194 and display 195 are connected to battery 33 (see FIG. 3) whereby battery 33 supplies the necessary power to microphone speaker assembly 194 and display 195. Battery 33 may be actuatable by a switch, such as switch 82 described above. Upon opening the casing, such as during a medical emergency, switch 82 is closed thereby allowing battery 33 to supply electrical power to the microphone speaker assembly 194 and display 195. The two way communication assembly may use GPS tracking device 190 (see FIG. 23) so as to cause medical kit 1 to initiate communications with local emergency personnel. Once a line of communication has been established, it is envisioned that medical kit 1 may be utilized to provide procedural instructions for the user, as well as streamlining the process of patient acceptance at a local medical center should the user need hospitalization.

Figure 27A:
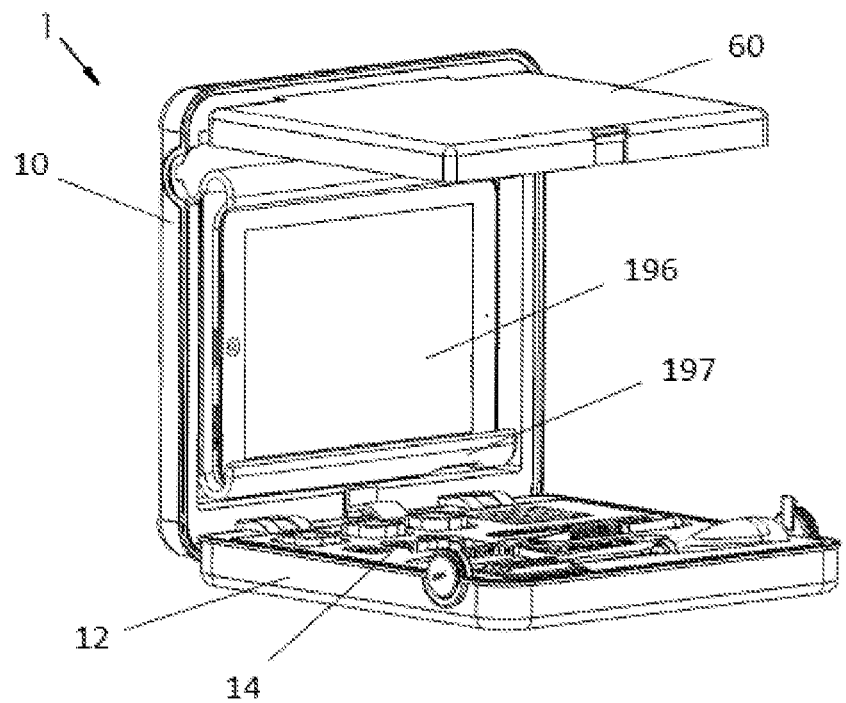
FIGS. 27A and 27B are perspective and front views of an embodiment on the medical tool kit according to the present invention with a tablet assembly comprising a tablet device and mounting hardware.
Figure 27B:
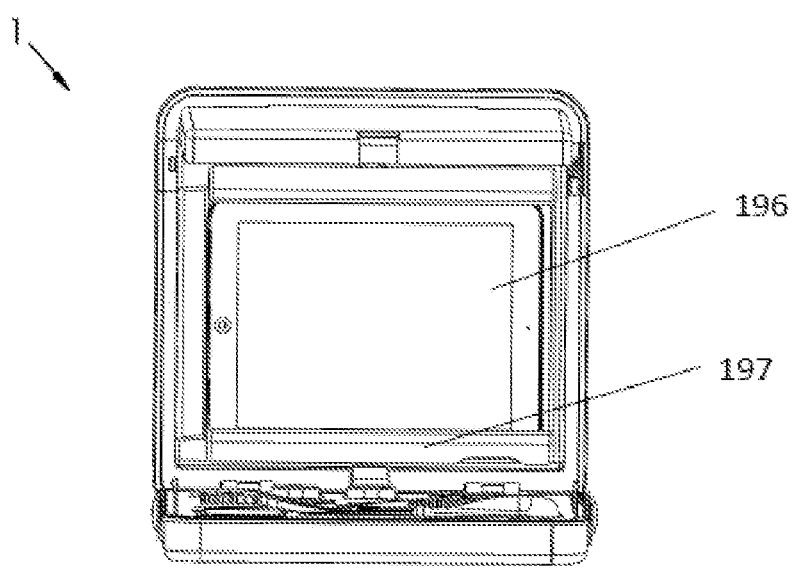
Figure 28:
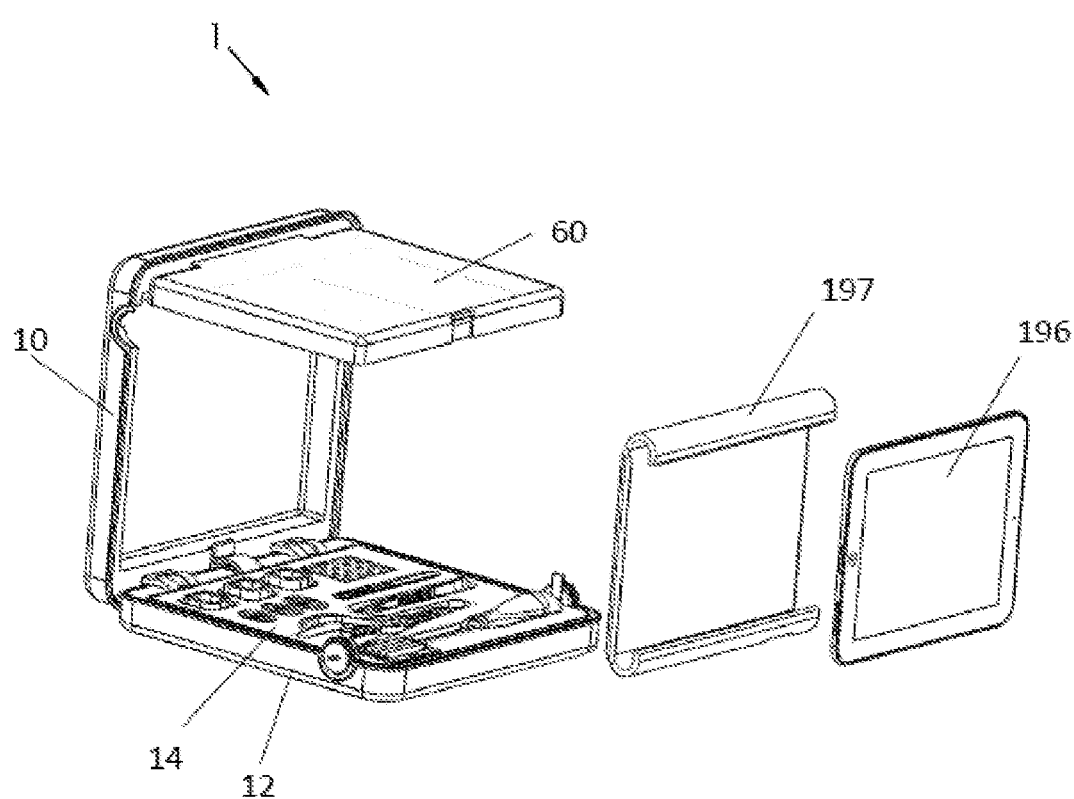
FIG. 28 is an exploded view of the embodiment of the medical tool kit shown in FIGS. 27A and 27B.

As shown in FIGS. 27A, 27B and 28, in accordance with a further aspect of the present invention, medical tool kit 1 may further comprise a tablet assembly comprising a tablet device 196 and associated mounting hardware 197. Tablet assembly may be comprised of tablet device 196 and tablet mounting hardware 197 wherein tablet mounting hardware 197 may be mounted to one or both of upper and lower casings 10, 12, with tablet device 196 removably secured within mounting hardware 197. Tablet mounting hardware 197 may comprise a pair of generally C-shaped brackets, each of which defines a channel adapted to receive tablet device 196. The channel may be dimensioned so as to be slightly larger than the width of tablet device 196 such that the tablet device resides snuggly within the channel. In one aspect of the present invention, each bracket is constructed of a rigid yet flexible material such that the channel may be flexed open a sufficient amount so as to enable insertion or removal of tablet device 196. In a further aspect of the present invention, tablet mounting hardware 197 is constructed of a rigid material such that tablet device 196 may be inserted or removed by sliding within the channel.

The tablet device 196 may be configured to include microphone speaker assembly 194 and touch screen display 195 which are configured for wireless communication similar to the medical tool kit described above with regard to FIGS. 26A and 26B. Tablet device 196 may further incorporate GPS device 190 (FIG. 23), and battery 33 (FIG. 3). Upon opening the casing, such as during a medical emergency as described above, switch 82 (see FIG. 11) may be closed so as to thereby supply electrical power to the tablet device 196. Alternatively, tablet device 196 may include a dedicated tablet battery which may be powered on via an actuator/switch (not shown) resident on tablet device 196. Tablet device 196 may further be configured to include a memory storage device, a central processing unit (CPU) and associated. In cases where wireless communications are inoperable or should microphone speaker assembly 194 and/or touch screen display 195 be unable to establish a wireless communication connection, medical procedure information may be accessed via tablet device 196 by accessing stored data from the memory storage device using touch screen display 195 or other input device known in the art (not shown) In accordance with this aspect of the present invention, tablet device 196 is envisioned to be an Apple iPad, Microsoft Surface or Samsung Galaxy or similar electronic device.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A medical kit, comprising:
   a case housing comprising a first housing part and a second housing part, wherein the first and second housing parts are movable relative to each other between a closed position and an open position, one of the first and second housing parts being configured to hold at least one medical instrument, tool, or supply;
   a seal sealing an interior of the housing when the first and second housing parts are in the closed position, so that contamination of the at least one medical tool, instrument, or supply is prevented by the seal, whereby a sterile state of the at least one medical instrument, tool, or supply is maintained while the case remains in the closed position;
   a UV lamp arranged in the case housing and actuatable when the housing is opened from the closed position to maintain the sterile state of the at least one medical instrument, tool, or supply when the case is in the open position; and
   a global positioning system (GPS) tracking device.

2. The medical kit of claim 1, further comprising a lamp assembly connected to one of the first and second housing parts, the UV lamp being part of the lamp assembly.

3. The medical kit of claim 2, wherein the lamp assembly is pivotally mounted to the one of the first and second housing parts so that the lamp assembly is pivotable from a storage position to an operable position in which the UV radiation is directed onto the at least one medical tool, instrument, or supply.

4. The medical kit of claim 3, wherein the lamp assembly is pivotally mounted to the second housing part.

5. The medical kit of claim 4, wherein the lamp assembly is held in the storage position against the second housing part in the closed position of the case housing and the lamp assembly pivots away from the second housing part when the housing is open to the operable position in which the UV radiation from the UV lamp is directed onto the at least one medical instrument, tool, or supply.

6. The medical kit of claim 5, further comprising a switch controlling the UV lamp and configured to actuate the UV lamp when the lamp assembly is proximate the operable position.

7. The medical kit of claim 5, further comprising a latch that holds the lamp assembly in the storage position until the housing is open to a predetermined extent, the latch being actuated when the housing is opened to the predetermined extent to release the lamp assembly, thereby allowing the lamp assembly to pivot away from the second housing part.

8. The medical kit of claim 1, further comprising a switch controlling the UV lamp and GPS tracking device, the switch configured to actuate the UV lamp and GPS tracking device when the case housing is proximate the open position.

9. The medical kit of claim 1, further comprising an aerosol sprayer containing an antiseptic material.

10. The medical kit of claim 9, wherein the aerosol sprayer is automatically actuatable to spray the at least one medical tool or supply when the housing is opened from the closed position.

11. The medical kit of claim 1, further comprising first and second liners inserted in said first and second housing parts, respectively.

12. The medical kit of claim 11, wherein said seal is arranged between rims of said first and second housing parts.

13. The medical kit of claim 11, wherein a tray holding said at least one medical tool, instrument, or supply is held in one of said first and second liners.

14. The medical kit of claim 1, further comprising a light assembly mounted on the exterior of one or both of said first and second housing parts.

15. The medical kit of claim 1, further comprising a handle assembly mounted on the exterior of one or both of said first and second housing parts.

16. The medical kit of claim 15, wherein said handle assembly is collapsible into a storage position within said one or both first and second housing parts wherein said lamp assembly is disabled when the handle assembly is in the storage position.

17. The medical kit of claim 1, further comprising a two way communication assembly.

18. The medical kit of claim 17, wherein the two way communication assembly comprises a microphone, speaker and display.

19. The medical kit of claim 1, further comprising a tablet assembly mounted on an interior portion of the other of said first and second housing parts.

20. The medical kit of claim 19, wherein the tablet assembly comprises a tablet device and a tablet mounting hardware wherein said tablet device is secured to said housing part using said tablet mounting hardware.

* * * * *